United States Patent
Bolton et al.

(10) Patent No.: US 10,221,210 B2
(45) Date of Patent: Mar. 5, 2019

(54) POLYPEPTIDE SEPARATION METHODS

(75) Inventors: Glen Reed Bolton, Boston, MA (US); Austin Wayne Boesch, Enfield, NH (US)

(73) Assignee: Zepteon, Incorporated, Enfield, NH (US)

( * ) Notice: Subject to any disclaimer, the term of this patent is extended or adjusted under 35 U.S.C. 154(b) by 0 days.

(21) Appl. No.: 13/554,501

(22) Filed: Jul. 20, 2012

(65) Prior Publication Data

US 2013/0084648 A1 Apr. 4, 2013

Related U.S. Application Data

(60) Provisional application No. 61/509,746, filed on Jul. 20, 2011.

(51) Int. Cl.
C07K 1/22 (2006.01)
(52) U.S. Cl.
CPC ..................... C07K 1/22 (2013.01)
(58) Field of Classification Search
CPC ....................................................... C07K 1/22
See application file for complete search history.

(56) References Cited

U.S. PATENT DOCUMENTS

| | | | | |
|---|---|---|---|---|
| 5,858,969 A * | 1/1999 | Marsh et al. | ................... | 514/1.5 |
| 2003/0175969 A1 | 9/2003 | Beliard et al. | | |
| 2007/0072307 A1* | 3/2007 | Godavarti et al. | ............ | 436/518 |
| 2007/0207500 A1* | 9/2007 | Bian et al. | ...................... | 435/7.1 |
| 2008/0167450 A1* | 7/2008 | Pan | ............................ | 530/387.3 |
| 2008/0312425 A1* | 12/2008 | Bonnerjea et al. | ............ | 530/413 |

FOREIGN PATENT DOCUMENTS

| | | | | |
|---|---|---|---|---|
| EP | 1 333 032 A1 | 8/2003 | | |
| WO | WO 9922764 A1 * | 5/1999 | ........... | A61K 39/395 |
| WO | WO 2008/057683 A2 | 5/2008 | | |
| WO | WO 2008/128225 A1 | 10/2008 | | |
| WO | WO 2009/018307 A2 | 2/2009 | | |
| WO | WO 2009027041 A1 * | 3/2009 | .............. | C12P 21/00 |
| WO | WO 2010/048313 A2 | 4/2010 | | |
| WO | WO 2011/017514 A1 | 2/2011 | | |
| WO | WO-2013057078 A1 | 4/2013 | | |

OTHER PUBLICATIONS

Raju, Terminal sugars of Fc glycans influence antibody effector functions of IgGs, Current Opinion in Immunology 2008, 20:471-479.*
Shields, Lack of Fucose on Human IgG1 N-Linked Oligosaccharides Improves Binding to FcγIII and Antibody-dependent Cellular Toxicity, The Journal of Biological Chemistry, 2002, 277:26733-26740.*
Wu et al., A Novel Polymorphism of FcγRIIIa (CD16) Alters Receptor Function and Predisposes to Autoimmune Disease, J. Clin. Invest. 100(5), 1997, 1059-1070.*
Niwa et al., Enhancement of the Antibody-Dependent Cellular Cytotoxicity of Low-Fucose IgG1 Is Independent of FcγRIIIa Functional Polymorphism, 10, 6248-6255, 2004.*
Alizadeh et al., Association analysis of functional variants of the FcgRIIa and FcgRIIIa genes with type 1 diabetes, celiac disease and rheumatoid arthritis, Human Molecular Genetics, 2007, 16(32), 2552-2559.*
Lowe CR, Combinatorial approaches to affinity chromatography, Curr Opin Chem Biol. Jun. 2001;5(3):248-56.
Li R, et al., Design, synthesis, and application of a protein A mimetic, Nat Biotechnol. Feb. 1998;16(2):190-5.
Okazaki A, et al., Fucose depletion from human IgG1 oligosaccharide enhances binding enthalpy and association rate between IgG1 and FcγRIIIa, J Mol Biol. Mar. 5, 2004;336(5):1239-49.
Ferrara C, et al., Unique carbohydrate-carbohydrate interactions are required for high affinity binding between FcγRIII and antibodies lacking core fucose, Proc Natl Acad Sci U S A. Aug. 2, 2011;108(31):12669-74.
Shibata-Koyama M, et al., The N-linked oligosaccharide at FcγRIIIa Asn-45: an inhibitory element for high FcγRIIIa binding affinity to IgG glycoforms lacking core fucosylation, Glycobiology Feb. 2009;19(2):126-34.
Kanda Y, et al., Comparison of biological activity among nonfucosylated therapeutic IgG1 antibodies with three different N-linked Fc oligosaccharides: the high-mannose, hybrid, and complex types, Glycobiology. Jan. 2006;17(1):104-18.
Bruhns P, et al., Specificity and affinity of human Fcγ receptors and their polymorphic variants for human IgG subclasses, Blood. Apr. 16, 2009;113(16):3716-25.
Lin CT, et al., Fc receptor-mediated signal transduction, J Clin Immunol. Jan. 1994;14(1):1-13.
Ghirlando R, et al., Stoichiometry and thermodynamics of the interaction between the Fc fragment of human $IgG_1$ and its low-affinity receptor FcγRIII, Biochemistry, Oct. 17, 1995;34(41):13320-27.
Nimmerjahn F and Ravetch JV, Divergent immunoglobulin g subclass activity through selective Fc receptor binding, Science. Dec. 2, 2005;310(5753):1510-12.
Van Mirre E, et al., Monomeric IgG in intravenous Ig preparations is a functional antagonist of FcγRII and FcγRIIIb, J Immunol. Jul. 1, 2004;173(1):332-9.
Ballerstadt R, et al. Concanavalin A for in vivo glucose sensing: A biotoxicity review. Biosensors and Bioelectronics, (2006) 22(2):275-284.
Carter P. Improving the efficacy of antibody-based cancer therapies. Nat Rev Cancer (2001) 1:118-129.
Chen S, et al., Aleuria Aurantia Lectin (AAL)—Reactive Immunoglobulin G Rapidly Appears in Sera of Animals following Antigen Exposure. PLoS One (2012) 7(9):e44422.
Chung S, et al., Quantitative evaluation of fucose reducing effects in a humanized antibody on Fcγ receptor binding and antibody-dependent cell-mediated cytotoxicity activities. mAbs (2012) 4(3):326-340.

(Continued)

Primary Examiner — Andrea S Grossman
(74) Attorney, Agent, or Firm — McCarter & English, LLP

(57) ABSTRACT

The present disclosure provides methods and compositions for separating polypeptide glycoforms using a medium that includes an Fc receptor. In certain embodiments, a medium includes an Fc receptor which comprises an extracellular portion of an Fc gamma RIII receptor.

57 Claims, 1 Drawing Sheet
Specification includes a Sequence Listing.

(56) References Cited

OTHER PUBLICATIONS

Daëron M., Fc Receptor Biology. Annual Review of Immunology (1997) 15(1):203-234.

Forthal DN, et al., Fc-Glycosylation Influences Fcγ Receptor Binding and Cell-Mediated Anti-HIV Activity of Monoclonal Antibody 2G12. The Journal of Immunology. (2010) 185;6876-6882.

Galon J, et al., Soluble Fcgamma receptor type III (FcgammaRIII, CD16) triggers cell activation through interaction with complement receptors. The Journal of Immunology (1996) 157(3):1184-1192.

Hulett MD, Hogarth PM, Molecular Basis of Fc Receptor Function. In: Frank JD, editor. Advances in Immunology: Academic Press. (1994) p. 1-127.

Jovanovic V, et al., Fcγ receptor biology and systemic lupus erythematosus. International Journal of Rheumatic Diseases (2009) 12(4):293-298.

Kanda Y, et al., Comparison of cell lines for stable production of fucose-negative antibodies with enhanced ADCC. Biotechnology and Bioengineering (2006) 94(4):680-688.

Lafont V, et al., Production of TNF-α by Human Vγ9Vδ2 T Cells via Engagement of FcγRIIIA, the Low Affinity Type 3 Receptor for the Fc Portion of IgG, Expressed upon TCR Activation by Nonpeptidic Antigen. The Journal of Immunology (2001) 166(12):7190-7199.

Malphettes L, et al., Highly efficient deletion of FUT8 in CHO cell lines using zinc-finger nucleases yields cells that produce completely nonfucosylated antibodies. Biotechnology and Bioengineering (2010) 106(5):774-783.

Niwa R, et al., IgG subclass-independent improvement of antibody-dependent cellular cytotoxicity by fucose removal from Asn297-linked oligosaccharides. J Immunol Methods (2005) 306:151-160.

Nose M, Wigzell H, Biological significance of carbohydrate chains on monoclonal antibodies. Proceedings of the National Academy of Sciences (1983) 80(21):6632-6636.

Satoh M, et al., Non-fucosylated therapeutic antibodies as next-generation therapeutic antibodies. Expert Opin Biol Ther (2006) 6:1161-1173.

Shields RL, et al., High Resolution Mapping of the Binding Site on Human IgG1 for FcgammaRI, Fcgamma RII, Fcgamma RIII, and FcRn and Design of IgG1 Variants with Improved Binding to the FcgammaR. Journal of Biological Chemistry (2001) 276: 6591-6604.

Shinkawa T, et al., The absence of fucose but not the presence of galactose or bisecting N-acetylglucosamine of human IgG1 complex-type oligosaccharides shows the critical role of enhancing antibody-dependent cellular cytotoxicity. J Biol Chem (2003) 278:3466-3473.

Sondermann P, et al., The 3.2-[angst] crystal structure of the human IgG1 Fc fragment-Fc[gamma]RIII complex. Nature (2000) 406(6793):267-273.

Sondermann P, et al., Molecular Basis for Immune Complex Recognition: A Comparison of Fc-Receptor Structures. Journal of Molecular Biology (2001) 309(3):737-749.

Tao MH, Morrison SL., Studies of aglycosylated chimeric mouse-human IgG. Role of carbohydrate in the structure and effector functions mediated by the human IgG constant region. The Journal of Immunology (1989) 143(8):2595-601.

Tojo S, et al., A Chromatographic Approach for Elevating the Antibody-Dependent Cellular Cytotoxicity of Antibody Composites. Biological and Pharmaceutical Bulletin (2009) 32(9):1604-1608.

Wagner C, Hänsch GM, Genetic deficiency of CD16, the low-affinity receptor for immunoglobulin G, has no impact on the functional capacity of polymorphonuclear neutrophils. European Journal of Clinical Investigation (2004) 34(2):149-155.

Wines BD, et al., The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A. The Journal of Immunology (2000) 164(10):5313-5318.

Ravetch, et al., Alternative Membrane Forms of FcγRIII(CD16) on Human Natural Killer Cells and Neutrophils Cell Type-Specific Expression of Two Genes That Differ in Single Nucleotide Substitutions J. Exp. Med. vol. 170 Aug. 1989 481-497.

Shibata-Koyama M, et al., Nonfucosylated rituximab potentiates human neutrophil phagocytosis through its high binding for FcgammaRIIIb and MHC class II expression on the phagocytotic neutrophils. Exp Hematol. (2009) 37(3):309-21.

Herbst R, et al., B-cell depletion in vitro and in vivo with an afucosylated anti-CD19 antibody. J Pharmacol Exp Ther. (2010); 335(1):213-22.

Rogers KA, et al., IgG Fc receptor III homologues in nonhuman primate species: genetic characterization and ligand interactions J Immunol. Sep. 15, 2006;177(6):3848-56.

Bux J, et al. Characterization of a new alloantigen (SH) on the human neutrophil Fc gamma receptor IIIb. Blood. (1997) 89(3):1027-34.

Roopenian DC, Akilesh S. FcRn: the neonatal Fc receptor comes of age. Nat Rev Immunol. (2007) 7(9):715-25.

Sondermann, P., et al. Characterization and crystallization of soluble human Fc gamma receptor II (CD32) isoforms produced in insect cells. *Biochemistry* (1999) 38:8469-8477.

Chesla, S.E., et al., The membrane anchor influences ligand binding two-dimensional kinetic rates and three-dimensional affinity of FcgammaRIII (CD16). *J Biol Chem* (2000) 275:10235-10246.

Vance, B.A., et al., Binding of monomeric human IgG defines an expression polymorphism of Fc gamma RIII on large granular lymphocyte/natural killer cells. *J Immunol* (1993) 151:6429-6439.

Salmon, J.E., et al., Fc gamma receptor III on human neutrophils. Allelic variants have functionally distinct capacities. *J Clin Invest* (1990) 85:1287-1295.

Kurlander, R.J., and Batker, J. The binding of human immunoglobulin G1 monomer and small, covalently cross-linked polymers of immunoglobulin G1 to human peripheral blood monocytes and polymorphonuclear leukocytes. *J Clin Invest* (1982) 69:1-8.

Ferrara, C., et al., The carbohydrate at FcgammaRIIIa Asn-162. An element required for high affinity binding to non-fucosylated IgG glycoforms. *J Biol Chem* (2006) 281:5032-5036.

Maenaka, K., et al. The human low affinity Fcgamma receptors IIa, IIb, and III bind IgG with fast kinetics and distinct thermodynamic properties. *J Biol Chem* (2001) 276:44898-44904.

Radaev, S., and Sun, P.D. Recognition of IgG by Fcgamma receptor. The role of Fc glycosylation and the binding of peptide inhibitors. *J Biol Chem* (2001) 276:16478-16483.

Powell, M.S., et al., Biochemical analysis and crystallisation of Fc gamma RIIa, the low affinity receptor for IgG. *Immunol Lett* (1999) 68:17-23.

Li P, et al., Affinity and Kinetic Analysis of Fc Receptor IIIa (CD16a) Binding to IgG Ligands, J. Biol. Chem (2007) 282(9) 6210-6221.

Nimmerjahn, et al., FcgammaRIV: A Novel FcR with Distinct IgG Subclass Specificity; Immunity, (2005) vol. 23, 41-51.

Huizinga, T, et al. Binding Characteristics of Dimeric Igg Subclass Complexes to Human Neutrophils, The Journal of Immunology (1989) vol. 142. 2359-2364. No. 7.

Ferrara, C, et al. Modulation of Therapeutic Antibody Effector Functions by Glycosylation Engineering: Influence of Golgi Enzyme Localization Domain and Co-Expression of Heterologous b1, 4-N-acetylglucosaminyltransferase III and Golgi a-Mannosidase II, Biotechnology and Bioengineering, vol. 93, No. 5, Apr. 5, 2006 pp. 851-861.

Taylor, RF A Comparison of Various Commercially-Available Liquid Chromatographic Supports for Immobilization of Enzymes and Immunoglobulins. Anal Chim Acta (1985) 172:241-248.

Umana, et al., Engineered Glycoforms of an Antineuroblastoma IgG1 With Optimized Antibody dependent Cellular Cytotoxic Activity, Nature Biotechnology vol. 17 Feb. 1999, pp. 176-180.

Jefferis, Antibody therapeutics: isotype and glycoform selection, Expert OPip. Bio. Ther. (2007) 7(9): 1401-1413.

Jefferis, Recombinant antibody therapeutics: the impact of glycosylation on mechanisms of action, Trends Pharm. Sci. 30(7) 356-362.

Jefferis, Glycosylation as a strategy to improve antibody-based therapeutics Nat. Rev. Drug Disc (2009) vol. 8 pp. 226-234.

(56) References Cited

OTHER PUBLICATIONS

Crispin, et al. al., Carbohydrate and Domain Architecture of an Immature Antibody Glycoform Exhibiting Enhanced Effector Functions, J. Mol. Biol. (2009) 387, pp. 1061-1066.

Kobata, The N-Linked sugar chains of human immunoglobulin G: Their unique pattern, and their functional roles, Biochimica et Biophysica Acta 1780 (2008) 472-478.

Walsh & Jefferis, Post-translational modifications in the context of therapeutic proteins, Nature Biotechnology (2006) 24 (10) pp. 1241-1252.

Koene, et al. FcgammaRIIIa-158V/F Polymorphism Influences the Binding of IgG by Natural Killer Cell FcgammaRIIIa, Independently of the FcgammaRIIIa-48L/R/H Phenotype, Blood (1997) 90: 1109-1114.

Dall'Ozzo, et al., Rituximab-Dependent Cytotoxicity by Natural Killer Cells: Influence of FCGR3A Polymorphism on the Concentration-Effect Relationship, Cancer Res. (2004); 64: 4664-4669.

Nimmerjahn & Ravetch, Fcgamma Receptors: Old Friends and New Family Members; Immunity (2006) 24:19-28.

J. Biochem, TNF Receptor II Fusion Protein with Tandemly Repeated Fc Domains, Jan. 2011, 149(3): 337-346.

Nimmerjahn and Ravetch (2008) "Fcγ Receptors as regulators of immune responses," *Nat. Rev.* 8: 34-47.

Presta (2006) "Engineering of therapeutic antibodies to minimize immunogenicity and optimize function", *Adv. Drug Deliv.* Rev. 58: 640-56.

Olovnikova (2012) "Anti-RhD-Mediated Immunosuppression: Can Monoclonal Antibodies Imitate the Action of Polyclonal Antibodies", in *Immunosuppression—Role in Health and Diseases*, Dr. Suman Kapur (Ed.), InTech, pp. 77-106.

Bruhns, Pierre et al.: "Specificity and affinity of human Fcγ receptors and their polymorphic variants for human IgG subclasses", *Blood*, Apr. 16, 2009, vol. 113, No. 16, pp. 3716-3725.

Mancardi, David A. et al.: "FcγRIV is a mouse IgE receptor that resembles macrophage FcεRI in humans and promotes IgE-induced lung inflammation", *The Journal of Clinical Investigation*, vol. 118, No. 11, Nov. 2008, pp. 3738-3750.

Ha et al. "Isolation and characterization of IgG1 with asymmetrical Fc glycosylation", *Glycobiology* 21(8): 1087-96 (2011).

Miller et al. "A Novel Role for the Fc Receptor γ Subunit: Enhancement of FcγR Ligand Affinity", *J. Exp. Med*. 183: 2227-33 (1996).

Iida, Shigeru et al.: "Nonfucosylated Therapeutic IgG1 Antibody Can Evade the Inhibitory Effect of Serum Immunoglobulin G on Antibody-Dependent Cellular Cytotoxicity through its High Binding to FcγRiIIa", *Clin. Cancer Res* 2006:12(9) May 1, 2006, pp. 2879-2887.

\* cited by examiner

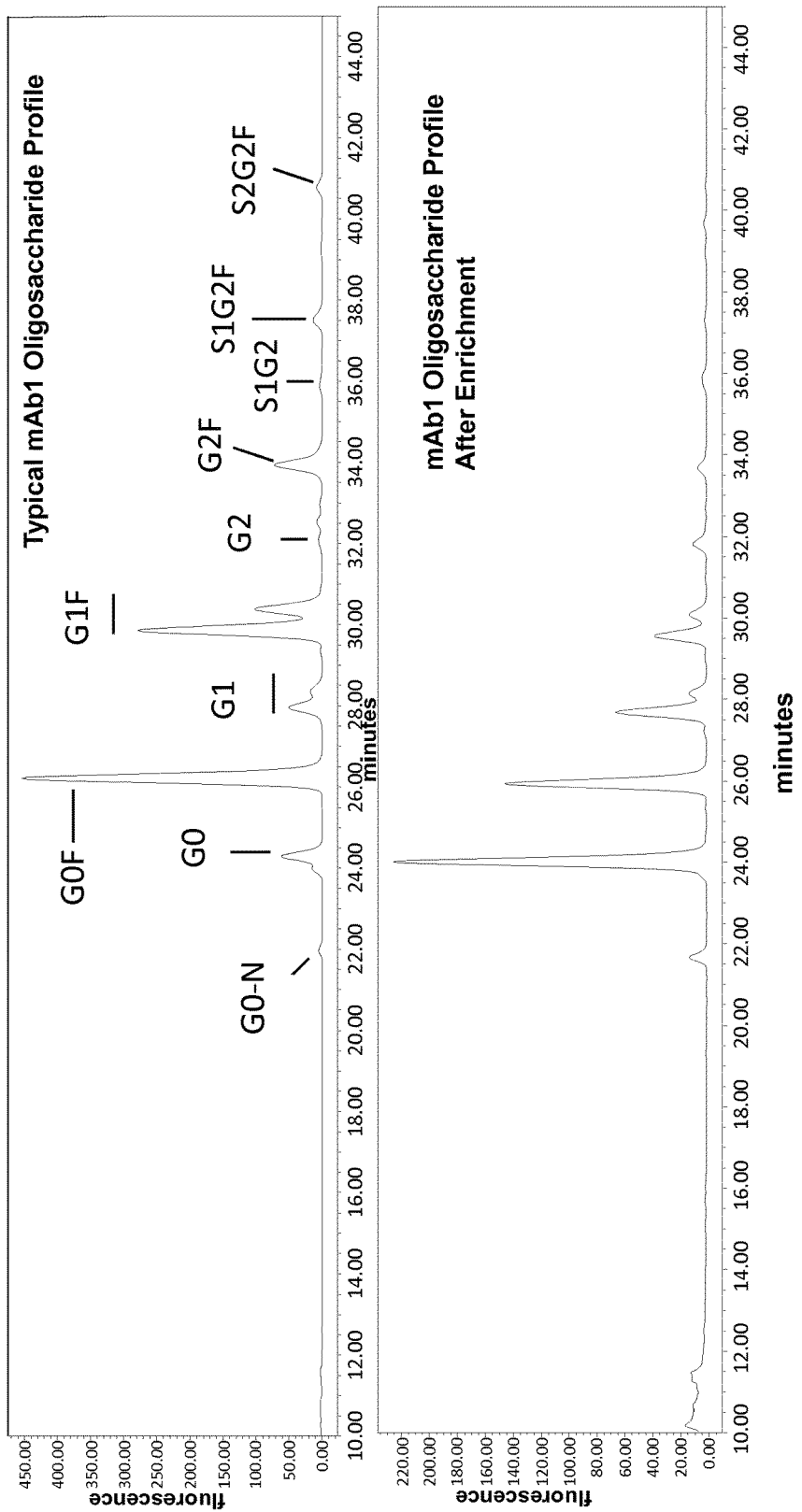

SEQUENCE LISTING

```
<160> NUMBER OF SEQ ID NOS: 16

<210> SEQ ID NO 1
<211> LENGTH: 254
<212> TYPE: PRT
<213> ORGANISM: Homo sapiens

<400> SEQUENCE: 1

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 2
<211> LENGTH: 233
<212> TYPE: PRT
<213> ORGANISM: Homo sapiens

<400> SEQUENCE: 2

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30
```

```
Gln Trp Tyr Ser Val Leu Glu Lys Asp Ser Val Thr Leu Lys Cys Gln
             35                  40                  45

Gly Ala Tyr Ser Pro Glu Asp Asn Ser Thr Gln Trp Phe His Asn Glu
 50                  55                  60

Ser Leu Ile Ser Ser Gln Ala Ser Ser Tyr Phe Ile Asp Ala Ala Thr
 65                  70                  75                  80

Val Asn Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
             100                 105                 110

Ala Pro Arg Trp Val Phe Lys Glu Glu Asp Pro Ile His Leu Arg Cys
             115                 120                 125

His Ser Trp Lys Asn Thr Ala Leu His Lys Val Thr Tyr Leu Gln Asn
130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
             180                 185                 190

Gly Leu Ala Val Ser Thr Ile Ser Ser Phe Ser Pro Pro Gly Tyr Gln
             195                 200                 205

Val Ser Phe Cys Leu Val Met Val Leu Leu Phe Ala Val Asp Thr Gly
             210                 215                 220

Leu Tyr Phe Ser Val Lys Thr Asn Ile
225                 230

<210> SEQ ID NO 3
<211> LENGTH: 5
<212> TYPE: PRT
<213> ORGANISM: Unknown
<220> FEATURE:
<223> OTHER INFORMATION: Description of Unknown: Recognition
      motif peptide
<220> FEATURE:
<221> NAME/KEY: MOD_RES
<222> LOCATION: (3)..(3)
<223> OTHER INFORMATION: Any amino acid

<400> SEQUENCE: 3

Leu Pro Xaa Thr Gly
 1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Gly Gly Gly
 1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 5

Cys Gly Gly Gly
1

<210> SEQ ID NO 6
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Lys Gly Gly Gly Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190

Val

<210> SEQ ID NO 7
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Cys Gly Gly Gly Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

```
Ser Asp Pro Val Gln Leu Glu Val His Ile Gly Trp Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190

Val

<210> SEQ ID NO 8
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Asp Leu Pro Lys Ala Val Val Phe Leu Glu Pro Gln Trp Tyr Arg
1               5                   10                  15

Val Leu Glu Lys Asp Ser Val Thr Leu Lys Cys Gln Gly Ala Tyr Ser
            20                  25                  30

Pro Glu Asp Asn Ser Thr Gln Trp Phe His Asn Glu Ser Leu Ile Ser
        35                  40                  45

Ser Gln Ala Ser Ser Tyr Phe Ile Asp Ala Ala Thr Val Asp Asp Ser
    50                  55                  60

Gly Glu Tyr Arg Cys Gln Thr Asn Leu Ser Thr Leu Ser Asp Pro Val
65                  70                  75                  80

Gln Leu Glu Val His Ile Gly Trp Leu Leu Leu Gln Ala Pro Arg Trp
                85                  90                  95

Val Phe Lys Glu Glu Asp Pro Ile His Leu Arg Cys His Ser Trp Lys
            100                 105                 110

Asn Thr Ala Leu His Lys Val Thr Tyr Leu Gln Asn Gly Lys Gly Arg
        115                 120                 125

Lys Tyr Phe His His Asn Ser Asp Phe Tyr Ile Pro Lys Ala Thr Leu
    130                 135                 140

Lys Asp Ser Gly Ser Tyr Phe Cys Arg Gly Leu Val Gly Ser Lys Asn
145                 150                 155                 160

Val Ser Ser Glu Thr Val Asn Ile Thr Ile Thr Gln Gly Leu Ala Val
                165                 170                 175

Ser Thr Ile Ser Ser Phe Phe Pro Pro Gly Tyr Gln Val His His His
            180                 185                 190

His His His His
        195

<210> SEQ ID NO 9
<211> LENGTH: 183
<212> TYPE: PRT
<213> ORGANISM: Homo sapiens
```

<400> SEQUENCE: 9

Ala Ala Pro Pro Lys Ala Val Leu Lys Leu Glu Pro Pro Trp Ile Asn
1               5                   10                  15

Val Leu Gln Glu Asp Ser Val Thr Leu Thr Cys Gln Gly Ala Arg Ser
                20                  25                  30

Pro Glu Ser Asp Ser Ile Gln Trp Phe His Asn Gly Asn Leu Ile Pro
            35                  40                  45

Thr His Thr Gln Pro Ser Tyr Arg Phe Lys Ala Asn Asn Asn Asp Ser
        50                  55                  60

Gly Glu Tyr Thr Cys Gln Thr Gly Gln Thr Ser Leu Ser Asp Pro Val
65                  70                  75                  80

His Leu Thr Val Leu Ser Glu Trp Leu Val Leu Gln Thr Pro His Leu
                85                  90                  95

Glu Phe Gln Glu Gly Glu Thr Ile Met Leu Arg Cys His Ser Trp Lys
            100                 105                 110

Asp Lys Pro Leu Val Lys Val Thr Phe Phe Gln Asn Gly Lys Ser Gln
        115                 120                 125

Lys Phe Ser His Leu Asp Pro Thr Phe Ser Ile Pro Gln Ala Asn His
130                 135                 140

Ser His Ser Gly Asp Tyr His Cys Thr Gly Asn Ile Gly Tyr Thr Leu
145                 150                 155                 160

Phe Ser Ser Lys Pro Val Thr Ile Thr Val Gln Val Pro Ser Met Gly
                165                 170                 175

Ser Ser Ser Pro Met Gly Ile
            180

<210> SEQ ID NO 10
<211> LENGTH: 172
<212> TYPE: PRT
<213> ORGANISM: Homo sapiens

<400> SEQUENCE: 10

Ala Pro Pro Lys Ala Val Leu Lys Leu Glu Pro Gln Trp Ile Asn Val
1               5                   10                  15

Leu Gln Glu Asp Ser Val Thr Leu Thr Cys Arg Gly Thr His Ser Pro
                20                  25                  30

Glu Ser Asp Ser Ile Gln Trp Phe His Asn Gly Asn Leu Ile Pro Thr
            35                  40                  45

His Thr Gln Pro Ser Tyr Arg Phe Lys Ala Asn Asn Asn Asp Ser Gly
        50                  55                  60

Glu Tyr Thr Cys Gln Thr Gly Gln Thr Ser Leu Ser Asp Pro Val His
65                  70                  75                  80

Leu Thr Val Leu Ser Glu Trp Leu Val Leu Gln Thr Pro His Leu Glu
                85                  90                  95

Phe Gln Glu Gly Glu Thr Ile Val Leu Arg Cys His Ser Trp Lys Asp
            100                 105                 110

Lys Pro Leu Val Lys Val Thr Phe Phe Gln Asn Gly Lys Ser Lys Lys
        115                 120                 125

Phe Ser Arg Ser Asp Pro Asn Phe Ser Ile Pro Gln Ala Asn His Ser
130                 135                 140

His Ser Gly Asp Tyr His Cys Thr Gly Asn Ile Gly Tyr Thr Leu Tyr
145                 150                 155                 160

Ser Ser Lys Pro Val Thr Ile Thr Val Gln Ala Pro
                165                 170

```
<210> SEQ ID NO 11
<211> LENGTH: 273
<212> TYPE: PRT
<213> ORGANISM: Homo sapiens

<400> SEQUENCE: 11

Gln Val Asp Thr Thr Lys Ala Val Ile Thr Leu Gln Pro Pro Trp Val
1               5                   10                  15

Ser Val Phe Gln Glu Glu Thr Val Thr Leu His Cys Glu Val Leu His
            20                  25                  30

Leu Pro Gly Ser Ser Ser Thr Gln Trp Phe Leu Asn Gly Thr Ala Thr
        35                  40                  45

Gln Thr Ser Thr Pro Ser Tyr Arg Ile Thr Ser Ala Ser Val Asn Asp
    50                  55                  60

Ser Gly Glu Tyr Arg Cys Gln Arg Gly Leu Ser Gly Arg Ser Asp Pro
65                  70                  75                  80

Ile Gln Leu Glu Ile His Arg Gly Trp Leu Leu Leu Gln Val Ser Ser
                85                  90                  95

Arg Val Phe Thr Glu Gly Glu Pro Leu Ala Leu Arg Cys His Ala Trp
            100                 105                 110

Lys Asp Lys Leu Val Tyr Asn Val Leu Tyr Tyr Arg Asn Gly Lys Ala
        115                 120                 125

Phe Lys Phe Phe His Trp Asn Ser Asn Leu Thr Ile Leu Lys Thr Asn
    130                 135                 140

Ile Ser His Asn Gly Thr Tyr His Cys Ser Gly Met Gly Lys His Arg
145                 150                 155                 160

Tyr Thr Ser Ala Gly Ile Ser Val Thr Val Lys Glu Leu Phe Pro Ala
                165                 170                 175

Pro Val Leu Asn Ala Ser Val Thr Ser Pro Leu Leu Glu Gly Asn Leu
            180                 185                 190

Val Thr Leu Ser Cys Glu Thr Lys Leu Leu Leu Gln Arg Pro Gly Leu
        195                 200                 205

Gln Leu Tyr Phe Ser Phe Tyr Met Gly Ser Lys Thr Leu Arg Gly Arg
    210                 215                 220

Asn Thr Ser Ser Glu Tyr Gln Ile Leu Thr Ala Arg Arg Glu Asp Ser
225                 230                 235                 240

Gly Leu Tyr Trp Cys Glu Ala Ala Thr Glu Asp Gly Asn Val Leu Lys
                245                 250                 255

Arg Ser Pro Glu Leu Glu Leu Gln Val Leu Gly Leu Gln Leu Pro Thr
            260                 265                 270

Pro

<210> SEQ ID NO 12
<211> LENGTH: 198
<212> TYPE: PRT
<213> ORGANISM: Homo sapiens

<400> SEQUENCE: 12

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60
```

```
Val Asp Asp Ser Gly Glu Tyr Arg Cys Gln Thr Asn Leu Ser Thr Leu
 65                  70                  75                  80

Ser Asp Pro Val Gln Leu Glu Val His Ile Gly Trp Leu Leu Leu Gln
                 85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Phe
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190

His His His His His His
            195

<210> SEQ ID NO 13
<211> LENGTH: 189
<212> TYPE: PRT
<213> ORGANISM: Homo sapiens

<400> SEQUENCE: 13

Thr Glu Asp Leu Pro Lys Ala Val Val Phe Leu Glu Pro Gln Trp Tyr
 1               5                  10                  15

Ser Val Leu Glu Lys Asp Ser Val Thr Leu Lys Cys Gln Gly Ala Tyr
                 20                  25                  30

Ser Pro Glu Asp Asn Ser Thr Gln Trp Phe His Asn Glu Ser Leu Ile
            35                  40                  45

Ser Ser Gln Ala Ser Ser Tyr Phe Ile Asp Ala Ala Thr Val Asn Asp
        50                  55                  60

Ser Gly Glu Tyr Arg Cys Gln Thr Asn Leu Ser Thr Leu Ser Asp Pro
 65                  70                  75                  80

Val Gln Leu Glu Val His Ile Gly Trp Leu Leu Leu Gln Ala Pro Arg
                 85                  90                  95

Trp Val Phe Lys Glu Glu Asp Pro Ile His Leu Arg Cys His Ser Trp
            100                 105                 110

Lys Asn Thr Ala Leu His Lys Val Thr Tyr Leu Gln Asn Gly Lys Asp
        115                 120                 125

Arg Lys Tyr Phe His His Asn Ser Asp Phe His Ile Pro Lys Ala Thr
    130                 135                 140

Leu Lys Asp Ser Gly Ser Tyr Phe Cys Arg Gly Leu Val Gly Ser Lys
145                 150                 155                 160

Asn Val Ser Ser Glu Thr Val Asn Ile Thr Ile Thr Gln Gly Leu Ala
                165                 170                 175

Val Ser Thr Ile Ser Ser Phe Ser Pro Pro Gly Tyr Gln
            180                 185

<210> SEQ ID NO 14
<211> LENGTH: 198
<212> TYPE: PRT
<213> ORGANISM: Homo sapiens
```

```
<400> SEQUENCE: 14

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Phe
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190

His His His His His His
        195

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 15

His His His His His His His His His His
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 16

His His His His His His
1               5
```

POLYPEPTIDE SEPARATION METHODS

RELATED APPLICATIONS

This application claims the benefit of U.S. Provisional Application No. 61/509,746, filed Jul. 20, 2011, which is incorporated herein by reference in its entirety.

BACKGROUND

Most membrane and secretory proteins are glycosylated. In many cases, the presence and characteristics of oligosaccharides impact folding, stability, location, ligand interaction, and biological activity of glycoproteins. For example, antibodies typically have complex N-linked oligosaccharides. These can be highly heterogeneous due to variations in levels of fucose, mannose, galactose, N-acetylglucosamine, and/or sialic acid in complex oligosaccharide chains (Jefferis, Trends Pharm. Sci. 30(7):356-362, 2009).

Serum and recombinant antibodies typically contain a mixture of glycoforms. Certain antibody glycoforms have been observed to have a higher affinity for Fc receptors on leukocytes such as Fc gamma RI, Fc gamma RII, Fc gamma RIII, and C1q, which in turn can alter effector function. Antibodies with oligomannose-type oligosaccharides display enhanced antibody dependent cell mediated cytotoxicity (ADCC) and reduced C1q binding (Crispin et al., J. Mol. Biol. 387:1061-1066, 2009). Removal of galactosylation reduces C1q binding and binding to other Fc receptors (Crispin et al., supra; Kobata, Biochim. Biophys. Acta 1780:472-478, 2008). Terminal sialic acids have been shown to reduce the affinity of antibodies for Fc gamma receptors (Jefferis, Nat. Rev. Drug. Disc. 8:226-234, 2009; Walsh et al., Nat. Biotech. 24(10):1241-1252, 2006).

Antibody forms lacking fucose on the primary core N-acetylglucosamine have increased affinity for Fc gamma RIIIa as compared to core-fucosylated forms, and also have an increased ability to trigger ADCC (Jefferis, Exp. Opin. Biol. Ther. 7(9):1401-1413, 2007; Okazaki et al., J. Mol. Biol. 336:1239-1249, 2004; Shibata-Koyama et al., Glycobiol. 19(2): 126-134, 2009). Afucosylated forms have comparable affinity for antigen, C1q, Fc gamma RI, the neonatal Fc receptor (FcRn) and slightly higher affinity for Fc gamma RIIa and Fc gamma RIIb, as compared to fucosylated forms (Jefferis, Exp. Opin. Biol. Ther. 7(9):1401-1413, 2007; Satoh et al., Exp. Opin. Biol. Ther. 6(11):1161-1173, 2006; Kobata, supra). Afucosylated forms of rituximab and trastuzumab have enhanced in vitro and ex vivo ADCC (Jefferis, Exp. Opin. Biol. Ther. 7(9):1401-1413, 2007; Jefferis, Trends Pharm. Sci. 30(7):356-362, 2009; Satoh, supra). Fc gamma RI, Fc gamma RII, Fc gamma RIII, and C1q receptors have been reported to interact with the hinge or hinge proximal region of Fc polypeptides. The increased affinity of afucosylated IgG Fc for Fc gamma RIII may be due to a conformational change in the Fc that reduces steric inhibition of binding (Kobata, supra; Satoh, supra).

SUMMARY

The present disclosure provides, inter alia, methods and compositions for separating polypeptide glycoforms. In various embodiments of methods provided herein, polypeptides having Fc receptor binding moieties are separated using Fc receptor media that preferentially bind one or more polypeptide glycoforms. Separation of polypeptide glycoforms has a variety of applications such as in preparative methods, e.g., for preparing compositions having a desired glycoform profile, for enriching for particular glycoforms that possess desired biological and/or therapeutic activity, and analytical methods, e.g., to permit characterization of polypeptide preparations.

Glycosylation is implicated in function, stability, and other important aspects of polypeptide biochemistry. Benefits offered by the present technology may impact development, production, and use (e.g., therapeutic use) of polypeptide products. The ability to separate glycoforms allows greater control over product variable quality attributes, in turn facilitating consistent manufacturing, clinical/regulatory analysis, and, in some cases, impacting therapeutic efficacy.

Accordingly, in one aspect, the present disclosure provides a method of separating polypeptide glycoforms in a load fluid. The method includes, for example: (a) providing a medium comprising an immunoglobulin Fc receptor; (b) contacting the medium with a load fluid comprising a polypeptide under conditions in which the polypeptide binds to the immunoglobulin Fc receptor, wherein the polypeptide comprises an immunoglobulin Fc receptor binding moiety, wherein the load fluid comprises a plurality of glycoforms of the polypeptide, and wherein the Fc receptor preferentially binds one or more of the glycoforms; (c) contacting the medium with an elution solution under conditions in which bound polypeptide elutes from the medium; and (d) recovering bound polypeptide that elutes from the medium, thereby producing an eluate.

In some embodiments, an Fc receptor binds to a first glycoform with an affinity which is at least 2 fold, 5 fold, 10 fold, 20 fold, 30 fold greater, 40 fold, 50 fold, 100 fold, or 150 fold greater than the affinity with it binds to another glycoform.

In some embodiments, a method includes contacting the medium with one or more wash solutions, prior to contacting the medium with the elution solution.

In various embodiments, a method includes recovering polypeptide that flows through the medium.

In some embodiments, a medium is loaded at 1-3000% (e.g., 5-1900%, 5-100%, or 100-1900%) of its polypeptide capacity. A medium can be loaded at a capacity that allows selective depletion from the flow through of glycoforms that bind to the medium. For example, in some embodiments, levels of certain glycoforms, e.g., glycoforms having reduced levels of fucose (e.g., afucosylated glycoforms), in the flow through fraction are less than 95%, 90%, 75%, 50%, 25%, 10%, or 5% of the levels in the load material.

A load fluid can be from a variety of sources. In some embodiments, a load fluid comprises cell culture medium (e.g., crude or filtered cell culture medium, cell culture medium comprising cells, or cell culture medium from which cells are removed). In some embodiments, a load fluid comprises a fluid that has been purified by one or more of ion exchange chromatography (e.g., cation exchange, anion exchange), protein A chromatography, UF/DF, virus reduction filtration, hydrophobic interaction chromatography, hydroxyapatite chromatography, mixed mode chromatography, lectin chromatography, or a combination thereof. In other embodiments, a load fluid comprises a pharmaceutical drug product or drug substance.

An immunoglobulin Fc receptor binding moiety can include, for example, an immunoglobulin Fc region. In some embodiments, an Fc receptor binding moiety includes a native immunoglobulin Fc region, or a portion or variant thereof that retains ability to bind to an Fc receptor.

In some embodiments, the immunoglobulin Fc receptor is selected from the group consisting of: Fc gamma RIIIa V176, Fc gamma RIIIa F176, Fc gamma RIIIb NA1, Fc gamma RIIIb NA2, Fc gamma RIIa H131, Fc gamma RIIa R131, Fc gamma RIIb I232, and Fc gamma RIIb T232.

Methods can be used to separate glycoforms of a variety of polypeptides. In some embodiments, a polypeptide separated using a method comprises an antibody (e.g., a monoclonal antibody, a human monoclonal antibody, a human IgG, a human IgG1). In some embodiments, a polypeptide comprises an Fc fusion protein (e.g., an Fc fusion protein having a human Fc region). Polypeptides for separation according to methods herein include single domain antibodies, maxibodies, minibodies, intrabodies, small modular immunopharmaceuticals (SMIPs), IgG-scFv bispecific antibodies, antibody-peptide conjugates, antibody-drug conjugates, and Fc receptor binding polypeptides on a virus or virus capsid.

In some embodiments, a polypeptide for separation is produced in a mammalian cell. In some embodiments, a polypeptide is produced in a fungal cell (e.g., *Pichia Pastoris*), an insect cell, or a plant cell. In some embodiments, a polypeptide is produced in a CHO cell (e.g., GS-CHO, CHO-K1, or CHO-K1SV), an NSO cell, or an Sp2/0 cell.

An Fc receptor is one which preferentially binds to one or more glycoforms. In some embodiments, an Fc receptor preferentially binds to a glycoform having reduced fucose (e.g., afucosylated glycoforms, e.g., glycoforms having reduced core N-fucose).

In some embodiments, an Fc receptor preferentially binds to polypeptide glycoforms having increased high mannose oligosaccharides.

In some embodiments, an Fc receptor is glycosylated. For example, the Fc can be N-glycosylated.

In some embodiments, an Fc receptor includes an Fc binding portion of an Fc gamma RIII polypeptide (e.g., an Fc gamma RIIIa polypeptide, or an Fc gamma RIIIb polypeptide) or an Fc gamma RIV polypeptide.

For example, the Fc receptor includes an extracellular domain of an Fc gamma RIII polypeptide or an Fc gamma RIV polypeptide; e.g., an Fc receptor comprises a sequence at least 85% identical to amino acid residues 21-209 of SEQ ID NO:1. In some embodiments, an extracellular domain of a Fc gamma RIII polypeptide is a V176 allotype.

In some embodiments, an Fc receptor comprises a full length Fc gamma RIII polypeptide.

In various embodiments of a method provided herein, a load fluid comprises a first glycoform that preferentially binds to the Fc receptor, and the percentage of the first glycoform in the eluate is increased by at least 20%, relative to the load fluid, e.g., the percentage of the first glycoform in the eluate is increased by at least 50%, 100%, 2-fold, 5-fold, 10-fold, or 20-fold, relative to the load fluid.

A method can enrich for a glycoform such that the eluate contains at least a given percentage. For example, in some embodiments, the percentage of the first glycoform in the eluate is at least 5%, 10% 20%, 30%, 40%, 45%, 50%, 55%, 60%, 65%, 70%, 75%, or 80%.

In some embodiments, the first glycoform is a glycoform having reduced fucose (e.g., an afucosylated glycoform).

In some embodiments, the first glycoform is a glycoform having reduced sialylation (e.g., an asialylated glycoform).

In some embodiments, the first glycoform is a galactosylated glycoform.

In some embodiments, the first glycoform is a glycoform having high mannose oligosaccharides.

An eluate can be collected or divided into fractions, one or more of which may be enriched for a particular glycoform.

In some embodiments of a method, a load fluid includes a second glycoform that does not preferentially bind to the Fc receptor, and the percentage of the second glycoform in the eluate is decreased, relative to the load fluid (e.g., wherein the second glycoform is a fucosylated, sialylated, and/or high mannose glycoform).

In some embodiments, a biological activity of polypeptide in the eluate is altered (e.g., increased or decreased) relative to the activity of the polypeptide in the load fluid. In some embodiments, a biological activity includes antibody dependent cell mediated cytotoxicity (ADCC). In some embodiments of a method, ADCC is increased (e.g., ADCC is increased by at least 20%, 50%, 100%, 2-fold, 5-fold, 10-fold, 20-fold, or 50-fold).

In some embodiments, a biological activity of polypeptide that has flowed through the medium is altered (e.g., increased or decreased), relative to the activity of the polypeptide in the load fluid.

Any of a variety of media can be used. In some embodiments, a medium comprises beads, membranes, monoliths, a fiber matrix, porous media, or a gel. In some embodiments, a medium comprises agarose, cellulose, or dextran, ceramic, metal, glass, nylon, TEFLON® (polytetrafluoroethylene), nylon, polycarbonate, polyacrylamide, polystyrene, polypropylene, polyether sulfone, polyamide, polytetrafluoroethylene, polysulfone, polyester, polyvinylidene fluoride, a fluorocarbon (e.g. poly(tetrafluoroethylene-co-perfluoro (alkyl vinyl ether)), polyethylene, polyacrylate, or poly (azolactone).

An Fc receptor can be linked to a medium via a crosslinker.

In some embodiments, an Fc receptor is linked to a medium via a disulfide bond, metal chelation, cyanogen bromide, an NHS linkage, a histidine tag, a glycidyl ether, an epoxy, a tresyl chloride linkage, a tosyl chloride linkage, an EAH linkage, an ECH linkage, an activated thiol linkage, or a thiopropyl linkage.

A medium comprises an Fc receptor, for example, at a concentration of 0.01 to 15 mg/mL. In some embodiments, a medium comprises an Fc receptor at a concentration between 2-10 mg/mL (e.g., between 3-7.5 mg/mL, 3-5 mg/mL, or 5-7.5 mg/mL).

In some embodiments, a medium is equilibrated with an equilibration solution prior to contacting the medium with the load fluid. In many embodiments, an equilibration solution includes a buffer (e.g., Tris, MES, HEPES, Phosphate, Histidine) between 1 and 500 mM, and a salt (e.g., NaCl, $CaCl_2$) between 0 and 2000 mM, at a pH between 3.5 and 10.

In various embodiments, a load fluid comprises a polypeptide at a concentration between 0.001 and 100 mg/mL. The amount of polypeptide contacted with the medium can range from 0.1 to 25,000 mg polypeptide/mL medium.

In some embodiments, one or more wash solutions used in a method include a buffer (e.g., Tris, MES, HEPES, Phosphate, Histidine) between 1 and 500 mM, and a salt (e.g., NaCl, $CaCl_2$) between 0 and 2000 mM, and/or an additive (e.g., guanidine, urea, sucrose) and/or a solvent (e.g., ethanol, acetonitrile, polyethylene glycol) at a pH between 3.5 and 10.

In some embodiments, an elution solution has a pH between 2 and 5 and or a salt (e.g., NaCl, $CaCl_2$) between 0 and 2000 mM, and/or an additive (e.g., guanidine, urea, sucrose) and/or a solvent (e.g., ethanol, acetonitrile, polyethylene glycol).

In some embodiments, a medium is contacted with one or more elution solutions under conditions in which a pH gradient is applied (e.g., a pH gradient from pH 5.0 to pH 3.0).

A method can further include neutralizing an eluate.

A separation method can be used in conjunction with other separation methods. Thus, in some embodiments, a method further includes contacting an eluate with a second medium, and recovering polypeptide that flows through, or is eluted from, the second medium. An exemplary second medium can include an ion exchange medium, a hydroxyapatite medium, a protein A medium, a hydrophobic interaction medium, an immobilized metal affinity medium, a synthetic medium (biomimetic), a lectin, or a combination thereof.

A method can further include producing a pharmaceutical composition from polypeptide in an eluate or from polypeptide that has flowed through the medium.

A method can further include analyzing a characteristic of polypeptide eluted from the medium. In some embodiments, oligosaccharides from the polypeptide are analyzed (e.g., N-linked oligosaccharides are analyzed by cleaving N-oligosaccharides from the polypeptide, labeling the oligosaccharides, and detecting labeled oligosaccharide species).

In some embodiments, a biological activity of polypeptide is analyzed.

In some embodiments, one or more of toxicity, stability (e.g., half life, shelf life), or efficacy are analyzed (e.g., as compared to polypeptide in the load fluid, polypeptide that has flowed through the medium, or as compared to a reference).

Analyzing can further include analyzing polypeptide in the load fluid and/or polypeptide that has flowed through the medium (e.g., for comparison with eluted polypeptide).

Alternatively, or in addition, a method can further include analyzing polypeptide that has flowed through the medium.

In some embodiments, oligosaccharides on the polypeptide are analyzed.

In some embodiments, one or more of toxicity, stability (e.g., half life, shelf life), or efficacy are analyzed (e.g., as compared to polypeptide in the load fluid, polypeptide that has eluted from the medium, or as compared to a reference).

In some embodiments, a biological activity of polypeptide is analyzed.

The present disclosure also features a composition including a polypeptide recovered by a method described herein.

In another aspect, the present disclosure provides a method that includes: (a) providing a medium comprising an Fc receptor, wherein the Fc receptor comprises an Fc binding portion of an Fc gamma RIII polypeptide; (b) contacting the medium with a load fluid comprising a polypeptide under conditions in which the polypeptide binds to the medium, wherein the polypeptide comprises an immunoglobulin Fc region; (c) contacting the medium with an elution solution under conditions in which bound polypeptide elutes from the medium; and (d) recovering bound polypeptide that elutes from the medium, thereby producing an eluate.

In some embodiments, an Fc receptor comprises an extracellular domain of an Fc gamma RIII polypeptide.

The method can include additional features described herein.

In some embodiments of the methods summarized above, the load fluid may comprise serum IgG.

In a further aspect, the present disclosure provides a medium comprising an Fc receptor linked to a solid support, wherein the Fc receptor comprises an Fc binding portion of an Fc gamma RIII polypeptide.

In some embodiments, a solid support comprises agarose, cellulose, or dextran, ceramic, metal, glass, nylon, TEFLON® (polytetrafluoroethylene), nylon, polycarbonate, polyacrylamide, polystyrene, polypropylene, polyether sulfone, polyamide, polytetrafluoroethylene, polysulfone, polyester, polyvinylidene fluoride, a fluorocarbon (e.g. poly (tetrafluoroethylene-co-perfluoro(alkyl vinyl ether)), polyethylene, polyacrylate, or poly(azolactone).

In some embodiments, a solid support comprises beads, membranes, monoliths, a fiber matrix, porous media, or a gel.

In another aspect, the present disclosure provides a kit that comprises (a) a medium comprising an immunoglobulin Fc receptor linked to a solid support, wherein the immunoglobulin Fc receptor comprises an Fc binding portion selected from the group consisting of: an Fc binding portion of an Fc gamma RI polypeptide, an Fc gamma RII polypeptide, an Fc gamma RIII polypeptide, and an Fc gamma RIV polypeptide; and (b) instructions for use according to any of the methods summarized above, such as the method, in accordance with one aspect of the present disclosure, of separating polypeptide glycoforms in a load fluid.

In some embodiments, the solid support of the kit comprises agarose, cellulose, or dextran, ceramic, metal, glass, nylon, TEFLON® (polytetrafluoroethylene), nylon, polycarbonate, polyacrylamide, polystyrene, polypropylene, polyether sulfone, polyamide, polytetrafluoroethylene, polysulfone, polyester, polyvinylidene fluoride, a fluorocarbon (e.g. poly(tetrafluoroethylene-co-perfluoro(alkyl vinyl ether)), polyethylene, polyacrylate, or poly(azolactone). The solid support may comprise beads, membranes, monoliths, a fiber matrix, porous media, or a gel.

Details of certain embodiments of the present disclosure are set forth in the accompanying drawing and the description below. Other features, objects, and advantages of the present disclosure will be apparent from the description and figures, and from the claims. All cited patents, and patent applications and references are incorporated by reference in their entireties for all purposes.

BRIEF DESCRIPTION OF THE FIGURE

FIG. 1 is a set of graphs depicting glycan profiles of a monoclonal antibody preparation (top panel) and the preparation which has been eluted from an Fc gamma RIIIa receptor medium (bottom panel). All peaks that have labels ending in 'F' are fucosylated and all peaks have labels that do not end in 'F' are afucosylated.

DEFINITIONS

"Corresponding": As used herein, an amino acid (or nucleotide) that is "corresponding" to an amino acid (or nucleotide) in a reference sequence occupies a site that is homologous to the site in the reference sequence. Corresponding amino acids and nucleotides can be identified by alignment of related sequences. Sequences can be compared to protein sequences available in public databases using algorithms such as BLAST, FASTA, ClustalW, which are well known to those skilled in the art.

An "eluate", as used herein, refers to a fluid that has been exposed to a medium and that has product eluted from the medium.

An "immunoglobulin Fc receptor" or "Fc receptor", as used herein, refers to a polypeptide that can interact with an immunoglobulin Fc region (e.g., a native Fc region). An Fc receptor typically binds to an Fc region with an affinity ($K_A$) of at least $10^5$ M$^{-1}$ (e.g., at least $10^6$-$10^9$ M$^{-1}$). In some embodiments, an Fc receptor comprises an extracellular portion of a native Fc gamma receptor, or a variant thereof having at least 80%, 85%, 90%, 95%, 96%, 97%, 98%, or 99% sequence identity to a native Fc gamma receptor.

An "immunoglobulin Fc receptor binding moiety" or "Fc receptor binding moiety", as used herein, refers to a moiety comprising amino acids that can interact with an immunoglobulin Fc receptor. In some embodiments, an Fc receptor binding moiety includes an Fc region. An Fc region is a C-terminal region of an immunoglobulin heavy chain, and generally comprises the last two constant region domains of an immunoglobulin, e.g., an IgG, IgA, or IgD, or the last three constant region domains of IgE or IgM. Camelid antibodies lack light chains but have Fc regions that are comparable to typical immunoglobulins. An Fc region can also include a flexible hinge region N-terminal to the constant region domains of an immunoglobulin. A human IgG heavy chain Fc region is usually defined to stretch from position C226 or P230 (according to Kabat numbering; see Kabat et al. *Sequences of Proteins of Immunological Interest*, 5$^{th}$ Ed. Public Health Service, National Institutes of Health, Bethesda, Md. (1991)) to the C-terminus of the molecule, although boundaries of an Fc region can vary. Amino acid and nucleic acid sequences of numerous Fc regions are known in the art.

In various embodiments, Fc receptor binding moieties include native Fc domains (e.g., native human Fc domains) and portions and variants thereof (e.g., variants having at least 80%, 85%, 90%, 95%, 96%, 97%, 98%, or 99% sequence identity to a native Fc domain) that bind to an Fc receptor. Antibodies and Fc fusion proteins are examples of polypeptides that include Fc receptor binding moieties.

A "load", as used herein, refers to any material containing a product of interest. A "load fluid" refers to a liquid containing load material for contact with a medium (e.g., liquid for passage through a column containing the medium). In some embodiments, a load fluid is a cell culture medium. A cell culture medium may be clarified (e.g., to remove cells or cell debris). In some embodiments, a load fluid is a partially purified intermediate derived from a chromatography step (e.g., a protein A chromatography step). In some embodiments, a load fluid is a purified preparation.

A "medium", as used herein, refers to any substance that can be used as a support for an Fc receptor for separation of polypeptide glycoforms.

"Preferentially binds", as used herein, e.g., to refer to Fc receptor interactions with glycoforms of Fc receptor binding moieties, means that the receptor binds to one glycoform more readily than it would bind to another glycoform (e.g., to one glycoform of a given polypeptide than to another glycoform of the same polypeptide). A receptor which "preferentially binds" to a given glycoform would more likely bind to that glycoform than to another glycoform, even though such a receptor may bind to the other glycoform. For example, a receptor may be considered to preferentially bind to a glycoform if it binds a first glycoform of a polypeptide with an affinity which is at least 50%, 100%, 2 fold, 5 fold, 10 fold, 20 fold, 30 fold, 40 fold, or 50 fold greater than the affinity with which it binds to a second glycoform of the polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

The term "nucleic acid" encompasses DNA, RNA (e.g., mRNA, tRNA), heteroduplexes, and synthetic molecules capable of encoding a polypeptide and includes all analogs and backbone substitutes such as PNA that one of ordinary skill in the art would recognize as capable of substituting for naturally occurring nucleotides and backbones thereof. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence.

Unless otherwise indicated, nucleic acids are written left to right in 5' to 3' orientation; amino acid sequences are written left to right in amino to carboxy orientation, respectively.

As used herein, the term "amino acid sequence" is synonymous with the terms "polypeptide," "protein," and "peptide," and are used interchangeably. Where such amino acid sequences exhibit activity, they may be referred to as an "enzyme." The conventional one-letter or three-letter code for amino acid residues are used herein.

As used herein, a "synthetic" molecule is produced by in vitro chemical or enzymatic synthesis rather than by an organism.

As used herein, the term "expression" refers to the process by which a polypeptide is produced based on the nucleic acid sequence of a gene. The process includes both transcription and translation.

A "gene" refers to the DNA segment encoding a polypeptide or RNA.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences in association therewith.

"Native" proteins or polypeptides refer to proteins or polypeptides isolated from the source in which the proteins naturally occur. "Recombinant" polypeptides refer to polypeptides produced by recombinant DNA techniques; e.g., produced from cells transformed by an exogenous DNA construct encoding the desired polypeptide. "Synthetic" polypeptides include those prepared by chemical synthesis as well as the synthetic antigens described above.

DETAILED DESCRIPTION OF CERTAIN EMBODIMENTS

Embodiments of the present invention may employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press. Each of these general texts is herein incorporated by reference.

Polypeptides for Separation

Methods and compositions provided herein can be used for separation of polypeptide glycoforms. Polypeptides that can be separated typically include an Fc receptor binding moiety (e.g., an immunoglobulin Fc region or portion thereof that binds to an Fc receptor). In some embodiments, polypeptides for separation include antibodies (e.g., monoclonal, polyclonal, chimeric, humanized, or human antibodies), Fc fusion proteins, antibody-drug conjugates, single domain antibodies, small modular immunopharmaceuticals (SMIPs), maxibodies, minibodies, intrabodies, scFv, IgG-scFv bispecific antibodies, or Fc-containing minibodies. Other types of polypeptides that bind to Fc receptors, Fc-receptor binding viral polypeptides, can also be separated.

In various embodiments, methods and compositions provided herein are used for separation of polypeptide glycoforms in monoclonal antibody preparations. In some embodiments, a therapeutic monoclonal antibody is separated. One class of therapeutic polypeptides for which the present disclosure is applicable is polypeptides whose therapeutic efficacy is thought to rely, at least in part, on the ability to trigger ADCC or CDC. In some embodiments, therapeutic polypeptides comprise human IgG antibodies. In some embodiments, human IgG antibodies are IgG1. In some embodiments, human IgG antibodies are IgG3. In some embodiments, human IgG antibodies are IgG4. In some embodiments, polypeptides comprise an Fc region of a human antibody, e.g. of a human IgG antibody (e.g., an IgG1, IgG3, or IgG4 antibody). In some embodiments, a polypeptide is a polypeptide (e.g., antibody) used to treat a cancer.

Polypeptides (e.g., antibodies) for separation according to methods provided herein include polypeptides that specifically bind to one or more of the following target molecules (with examples of polypeptides that bind these targets): the Aβ fragment of amyloid precursor protein (see, e.g., U.S. Pat. No. 7,625,560; e.g., bapineuzumab); HER2/neu receptor (e.g., trastuzumab); CD20 (e.g., rituximab, ofatumumab, afutuzumab, tositumomab); B cell activating factor (BAFF) (e.g., belimumab); TNFα (e.g., adalimumab, infliximab, etanercept, golimumab); CD52 (e.g., alemtuzumab); CD25 (e.g., basiliximab, daclizumab); VEGF (e.g., bevacizumab); EGFR (e.g., cetuximab, panitimumab, nimotuzumab); CD11a (e.g., efalizumab); CD33 (e.g., gemtuzumab); CD3; alpha-4 integrin (e.g., natalizumab); IgE (e.g., omalizumab); GDF-8 (see, e.g., U.S. Pat. Pub. No. 20040142382); IL-12R/IL-23R (p40)(e.g., ustekinumab); B7 (e.g., CTLA4-Ig, e.g., abatacept); complement C5 (e.g., eculizumab); platelet GpIIb/IIIa (e.g., abciximab); phosphatidylserine (e.g., bavituximab); and pF-RSV (palivizumab).

Polypeptides for separation according to methods described herein can be from any of a number of sources including, but not limited to, conditioned media derived from culturing a recombinant cell line that expresses a polypeptide, cell extracts of polypeptide-producing cells, serum (e.g., serum of an immunized subject, serum of a subject who has been exposed to an infectious agent, serum of a subject who has developed immunity to an infectious agent (e.g., either by immunization or natural exposure), serum of a naïve subject, human serum), ascites fluid, hybridoma or myeloma supernatants, commercially available polypeptide preparations (e.g., drug product), and other sources. In one embodiment of the present disclosure, partially purified polypeptide from conditioned cell culture media of a variety of polypeptide producing recombinant cells are separated.

In some embodiments, a polypeptide for separation or an Fc receptor for use in separating the polypeptide according to a method described herein is produced by expression in a recombinant cell. Nucleotide sequences encoding the polypeptide for separation or the Fc receptor may be inserted into vectors. The term "vector" is widely used and understood by those of ordinary skill in the art, and as used herein the term "vector" is used consistent with its meaning to those of ordinary skill in the art. For example, the term "vector" is commonly used by those ordinarily skilled in the art to refer to a vehicle that allows or facilitates the transfer of nucleic acid molecules from one environment to another or that allows or facilitates the manipulation of a nucleic acid molecule.

For example, a vector is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. When the polynucleotide encodes a polyprotein fragment, advantageously, in the vector, an initiation codon (ATG) is placed at 5' of the reading frame and a stop codon is placed at 3'. Other elements for controlling expression may be present, such as enhancer sequences, stabilizing sequences and signal sequences permitting the secretion of the protein. The transformed hosts can be fermented and cultured according to means known in the art to achieve optimal cell growth.

Any vector that allows expression of the polypeptides of the present disclosure may be used in accordance with embodiments of the present invention. In certain embodiments, the polypeptides of the present disclosure may be used in vitro (such as using cell-free expression systems) and/or in cultured cells grown in vitro. For such applications, any vector that allows expression of the polypeptides in vitro and/or in cultured cells may be used.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript.

Transcriptional and translational control sequences are DNA regulatory sequences, such as promoters, enhancers, ribosome binding sites, upstream regulatory domains, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes. Not all of these control sequences need always be present in a recombinant vector so long as the desired gene is capable of being transcribed and translated.

A "promoter sequence" is a DNA regulatory region capable of binding RNA polymerase in a cell and initiating transcription of a downstream (3' direction) coding sequence. The promoter sequence is typically bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

As used herein, "fragment" or "portion" as applied to a gene or a polypeptide, will ordinarily be at least 10 residues, more typically at least 20 residues, and preferably at least 30 (e.g., 50) residues in length, but less than the entire, intact sequence. Fragments of these genes can be generated by methods known to those skilled in the art, e.g., by restriction digestion of naturally occurring or recombinant fiber or fibritin genes, by recombinant DNA techniques using a vector that encodes a defined fragment of the fiber or fibritin gene, or by chemical synthesis.

A wide variety of cells can be used to produce a recombinant protein. Any cell that can be transformed with recombinant DNA to express a protein of interest (e.g., a monoclonal antibody), can be used in the methods of the present disclosure. Cells can be from a variety of species, e.g., eukaryotic species, including plant, yeast, nematode, worm, insect, amphibian, or mammal, for example, human, primate, ovine, bovine, porcine, equine, feline, canine, or rodent source. In particular embodiments, the cells are from human or rodent. In particular embodiments, the cells are from hamster (e.g., Chinese hamster ovary cells). Examples of mammalian cells that may be used include BALB/c mouse myeloma line (NSO/I, ECACC No: 85110503); SP2/0; Balb/c 3T3; human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells+/−DHFR (CHO, Urlaub and Chasin, Proc. Natl. Acad. Sci. USA, 77:4216 (1980); GS-CHO, CHO-K1, CHO-K1SV, CHO-DG44, CHO-DUKX, CHO-DUXB11, CHO-S); mouse sertoli cells (TM4, Mather, Biol. Reprod., 23:243-251 (1980)); rat hybridoma YB2/0 (Shinkawa et al., J. Biol. Chem. 278:3466-3473, 2003); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2). A number of suitable cell lines can be obtained from depositories such as the America Type Culture Collection (ATCC), Manassas, Va. Examples of plant cells that may be used include *Lemmna minor* (duckweed), *Arabidopsis thalania*, and *Physcomitrella patens* (moss) cells. Examples of insect cells that may be used include *Spodoptera frugiperda* (Sf9 and Sf21), *Trichoplusia ni* (Tni and BTI-Tn 5B1-4), and *Mamestra brassicae* (Mb) cells. Useful fungal cells include *Pichia pastoris* and *Saccharomyces cerevisiae* cells.

Methods described herein can permit selection and enrichment of polypeptide glycoforms from an initial preparation having any pattern of glycoform expression, without a need for selection of a specialized host cell or use of atypical conditions or preparative steps. However, it may, in some cases, be beneficial to apply methods to separation of preparations in which a expression of a glycoform is altered, e.g., so as to increase expression of a desired glycoform and/or decrease expression of an unwanted glycoform. Combinations of conditions and separation modes that favor enrichment of a glycoform of interest may permit isolation of glycoforms at higher levels of purity or with fewer steps than previously possible. In some embodiments, glycoform expression is altered by genetic manipulation of a host cell to have increased or decreased expression of an enzyme that participates a glycosylation pathway (e.g., an enzyme that catalyzes addition or trimming of carbohydrate moieties). Such modifications can include introduction, deletion, and/ or knocking down of a gene encoding a glycosyltransferase, e.g., an alpha-1,6-fucosyltransferase, or a glycosidase. Cells lacking expression of alpha-1,6-fucosyltransferase by way of disruption of the FUT8 gene are described, e.g., in Yamani-Ohnuki et al., Biotechnol. Bioeng. 87(5):614-622, 2004 and WO2009/009086 Cell variants that produce polypeptides having reduced fucosylation have been described (e.g., CHO Lec13 cells, Shields et al., J. Biol. Chem. 277(30):26733-26740, 2002; and CHO Ms704, Kanda et al. Biotech. Bioeng. 94(4):680-688, 2006).

Lower eukaryotic (e.g., fungal cells can be engineered to produce polypeptides with complex glycosylation characteristic of mammalian cells. See, e.g., Hamilton et al., Science 313:1441-1443, 2006, which describes *Pichia pastoris* engineered to produce complex terminally sialylated glycoproteins. See also WO2002/000879, WO2004/074458, WO2004/074499, WO2004/074498, and WO2005/100584. Plant cells (e.g., *Lemna minor*, or moss, can be engineered to produce polypeptides having desired glycoforms, e.g., lacking plantlike glycosylation (see, e.g., Cox et al., Nat. Biotech. 24:1591-1597, 2006 and Nechansky et al., Mol. Immunol. 44:1815-1817, 2007).

In some embodiments, a polypeptide is produced in a cell under conditions that alter glycosylation. For example, inclusion of 10-600 nM manganese in cell culture medium can result in a more extensive glycosylation pattern (U.S. Pat. Pub. 2008/0081356). In some embodiments, a polypeptide is produced in a cell in the presence of an agent that modulates glycosylation. For example, in some embodiments, an inhibitor or agonist of a carbohydrate modifying enzyme is used. In some embodiments, an inhibitor is a nucleic acid antagonist (e.g., siRNA). Glycosylation of polypeptides can be altered enzymatically in vitro (e.g., outside a cell), e.g., by treatment with a glycosyltransferase or glycosidase.

Binding Media

Fc Receptors

Fc receptors that can be used according to the present disclosure include receptors that preferentially bind to one or more polypeptide glycoforms. A receptor that preferentially binds to one or more polypeptide glycoforms binds with an affinity that is at least 50%, 100%, two fold (e.g., 5, 10, 20, 30, 40, 50, 75, 100, 150, or 200 fold) higher than an affinity with which it binds to another glycoform of the polypeptide. In some embodiments, an Fc receptor preferentially binds to glycoforms lacking or with reduced levels of fucose (e.g., glycoforms with low levels or the absence of core N-fucosylation; e.g., antibody glycoforms lacking fucose on one or both heavy chains). For example, the Fc receptor can include an extracellular portion of an Fc gamma RIII polypeptide (e.g., an Fc gamma RIIIa polypeptide, or an Fc gamma RIIIb polypeptide). In some embodiments, an Fc receptor preferentially binds glycoforms with reduced sialic acid. In some embodiments, an Fc receptor preferentially binds glycoforms containing high mannose. In some embodiments, an Fc receptor preferentially binds galactosylated glycoforms.

In certain further embodiments, the Fc receptor used according to the present disclosure includes Fc receptors that bind to polypeptide glycoforms lacking or with reduced levels of fucose (e.g., glycoforms with low levels or the absence of core N-fucosylation; e.g., antibody glycoforms lacking fucose on one or both heavy chains) with a $K_D$ that is three times, four times, five times, six times, seven times, eight times, nine times, or ten times smaller than the $K_D$ of the Fc receptor for the fucosylated form of the polypeptide. For examples of such binding affinities of suitable Fc receptors for use in some embodiments of the instant invention, see, e.g., Herbst, R et al. J. Pharmacol. Exp. Ther. 335(1):213-222 (2010) and Shibata-Koyama, M et al. Exp. Hematol. 37:309-321 (2007).

Accordingly, it has been surprisingly found by Applicants that Fc receptors that bind to certain glycoform polypeptides, such as afucosylated polypeptides, with $K_{off}$ rates of only about five to ten fold higher than other glycoforms can be used in affinity purification methods to purify the glycoform polypeptide, such as, for example, purifying afucosylated polypeptide forms from a mixture of different glycoform polypeptides. In a particular embodiment, an Fc receptor such as Fc gamma RIIIa has a binding affinity for afucosylated antibody forms that involves a $K_{off}$ rate of the afucosylated antibody for the Fc receptor that doesn't necessarily lend itself to affinity purification of the antibody, such as, for example, by affinity chromatography involving binding of the afucosylated antibody to the Fc receptor. In these embodiments, the afucosylated polypeptide stays bound to the Fc receptor such that it does not typically fall off during a wash with, for example, PBS buffer, but will come off when exposed to more stringent conditions, such as, for example, a pH gradient. For examples of $K_{off}$ rates of Fc receptor and glycoform antibody binding that surprisingly are amenable to purification by affinity chromatography according to some embodiments of the instant invention, see Li, P et al. J. Biol. Chem. 282(9):6210-6221 (2007).

Fc gamma RIIIa (also known as CD16a or FCGR3A protein) is a type I membrane protein that is naturally expressed both as a membrane protein and a soluble receptor produced by proteolytic cleavage. Full length Fc gamma RIIIa has two Ig-like C2-type domains in its extracellular region. Fc gamma RIIIa binds to the Fc region of IgGs. The structural association of a human Fc gamma RIII polypeptide with a human IgG1 Fc domain polypeptide has been characterized (Sondermann et al., Nature 406:267-273, 2000). Fc gamma RIIIa binds complexed, aggregated, and monomeric IgG. Fc gamma RIIIa mediates antibody-dependent cellular toxicity and other antibody-dependent responses such as phagocytosis. Depletion of fucose from IgG1 enhances its affinity for Fc gamma RIIIa and enhances its ability to cause ADCC (Okazaki et al., J. Mol. Biol. 336:1239-1249, 2004). In one study, an IgG1 bound to Fc gamma RIIIa (V176 allotype) with a $K_a=1.87\times10^6$ M$^{-1}$, and a defucosylated form of the IgG1 bound with a $K_a=58.3\times10^6$ M$^{-1}$, as measured using a BIAcore™ biosensor. Enhanced Fc gamma RIIIa affinity and ADCC has also been observed for defucosylated IgG2, IgG3, and IgG4 (Jefferis, Trends Pharm. Sci. 30(7):356-362, 2009). The oligosaccharide structure of Fc gamma RIIIa contributes to its enhanced binding to defucosylated antibody.

An exemplary amino acid sequence of a full length human Fc gamma RIIIa polypeptide is shown in SEQ ID NO:1 (see also Acc. No. P08637 of UniProt, on the world wide web at uniprot.org/uniprot/P08637). The signal peptide is at about amino acids 1-16. The extracellular domain is between amino acids 17-208. Ig-like domains are found between amino acids 24-105 and 107-189. Residues 230-254 are cytoplasmic. N-linked glycosylation may occur at residues 56, 63, 92, 180, and 187. When an oligosaccharide at position 180 is removed, the receptor has the same affinity for fucosylated and afucosylated IgG Fc (Jefferis, Nat. Rev. Drug. Disc. 8:226-234, 2009; Shibata-Koyama, supra). Removal of only the glycosylation at position 63 of Fc gamma RIIIa increases its affinity for afucosylated IgG. Removal of all glycosylation except that at position 180 increases affinity for afucosylated IgG (Shibata-Koyama, supra). Removal of all glycosylation except that at positions 180 and 63 results in an affinity for afucosylated IgG that is higher than the wild type Fc gamma RIIIa but lower than the affinity with glycosylation only at position 180 (Shibata-Koyama, supra).

1070, 1997). IgG1 is more efficient at mediating ADCC through Fc gamma RIIIa V176-bearing cells than Fc gamma RIIIa F176-bearing cells (Jeffries et al. Exp. Opin. Biol. Ther. 7(9):1401-1413, 2007).

Orthologs of human Fc gamma RIIIa have been identified, e.g., in *P. troglodytes* (see GenBank. Acc. No. XP_001174052.1), *M. mulatta* (see GenBank. Acc. No. NP_001041713.1), *M. fascicularis* (see GenBank Acc. No. NP_001106117.1), *P. anubis* (see GenBank. Acc. No. NP_001106117.1), *M. musculus* (see GenBank Acc. No. NP_653142.1), *R. norvegicus* (see GenBank. Acc. No. NP_997486.1), *B. Taurus* (see GenBank. Acc. No. NP_001070870.1), *C. lupus* (see GenBank. Acc. No. XP_536141.2), *Cercocebus torquatus atys* (Red-crowned mangabey) (Sooty mangabey) (see GenBank. Acc. No. DQ423376 mRNA. Translation: ABD83656.1), Papio anubis (Olive baboon) (see GenBank Acc. No. DQ423378 mRNA. Translation: ABD83658.1), and other species.

Fc receptors for use in media as described herein can include an extracellular portion of an Fc gamma RIIIa polypeptide that retains the ability to bind to a glycoform of an Fc-containing polypeptide. For example, an Fc receptor can have a sequence at least 80%, 85%, 90%, 95%, 96%, 97%, 98%, 99% identical to the extracellular domain of the sequence shown in SEQ ID NO:1, or a sequence at least 80%, 85%, 90%, 95%, 96%, 97%, 98%, 99% identical to a portion thereof (e.g., a portion comprising amino acids 21-209, amino acids 17-208, amino acids 21-192, amino acids 21-169, or amino acids 106-169 of SEQ ID NO:1). In various embodiments, an Fc receptor has a sequence which differs from one of these portions of an Fc gamma RIIIa sequence in at least 1 amino acid position, but not more than 15 amino acid positions (e.g., the sequence differs from amino acids 21-209 of SEQ ID NO:1 at 1, 2, 3, 4, 5, 6, 7, 8, 9, 10, 11, 12, 13, 14, or 15 amino acid positions). In various embodiments, an Fc receptor is glycosylated at a site corresponding to N180 in SEQ ID NO:1. In various embodiments, an Fc receptor lacks glycosylation at a site corresponding to N63 of SEQ ID NO:1 (e.g., due to substitution

TABLE 1

Exemplary full length Fc gamma RIIIa amino acid sequence

```
        10         20         30         40         50         60
MWQLLLPTAL LLLVSAGMRT EDLPKAVVFL EPQWYRVLEK DSVTLKCQGA YSPEDNSTQW 70         80         90        100        110        120
FHNESLISSQ ASSYFIDAAT VDDSGEYRCQ TNLSTLSDPV QLEVHIGWLL LQAPRWVFKE 130        140        150        160        170        180
EDPIHLRCHS WKNTALHKVT YLQNGKGRKY FHHNSDFYIP KATLKDSGSY FCRGLFGSKN 190        200        210        220        230        240
VSSETVNITI TQGLAVSTIS SFFPPGYQVS FCLVMVLLFA VDTGLYFSVK TNIRSSTRDW

250
KDHKFKWRKD PQDK
(SEQ ID NO: 1)
```

Post-translational modifications of Fc gamma RIIIa include high mannose and complex oligosaccharides (e.g., at residues 56, 63, 92, 180, and 187 of SEQ ID NO:1). Fc gamma RIIIa is polymorphic. Examples of natural amino acid allotypes include polypeptides having the following amino acid changes in SEQ ID NO:1: L66H, L66R, G147D, Y158H, F176V, and F203S. Allotypes having a valine at position 176 bind more strongly to IgG1, IgG3, and IgG4 than allotypes having a phenylalanine (Koene et al., Blood 90(3):1109-1114, 1997; Wu et al., J. Clin. Inv. 100(5):1059- of an asparagines residue). In various embodiments, an Fc receptor comprises amino acids 21-192 of SEQ ID NO:1, wherein F176 is changed to V176. In various embodiments, an Fc receptor comprises amino acids 21-192 of SEQ ID NO:1, wherein N63 is substituted for another amino acid (e.g., to glutamine, aspartic acid, or glutamic acid).

Fc gamma RIIIb (also known as CD16b or FCGR3B protein) is a glycoprotein that shares sequence similarity with Fc gamma RIIIa. Full length Fc gamma RIIIb has two Ig-like C2-type domains in its extracellular region. Fc gamma RIIIb is naturally expressed as a GPI-anchored form and a secreted form released by a proteolytic cleavage. Fucosylation decreases the affinity of some antibodies for Fc gamma RIIIb (Bruhns et al., Blood 113(16): 3716-3725, 2008).

An exemplary amino acid sequence of a full length human Fc gamma RIIIb polypeptide is shown in SEQ ID NO:2 (see also Acc. No. O75015 of UniProt, on the world wide web at uniprot.org/uniprot/075015). The signal peptide is at about amino acids 1-16. The extracellular domain is between amino acids 17-200. Ig-like domains are found between amino acids 40-96 and 121-179. Amino acids 201-233 may be removed in mature forms. N-linked glycosylation may occur at residues 56, 63, 82, 92, 180, and 187. Lipidation may occur at amino acid 200.

macaque (accession number, Q8SPW2). As described in Nimmerjahn and Ravetch, Fc gamma RIV requires gamma chain for its surface expression. Fc gamma RIV is highly expressed on neutrophils, monocytes, macrophages, and dendritic cells. It can be upregulated by inflammatory stimuli such as LPS and TH-1 cytokines such as IFN-gamma and can be downregulated by TH-2 cytokines such as IL-4 and IL-10 or TGF-beta. See Nimmerjahn, F and Ravetch, J V Immunity 24:19-28 (2006). Mouse Fc gamma RIV has similar affinity properties to human Fc gamma RIIIA in that the $K_D$ for afucosylated IgG is approximately ten times smaller than the $K_D$ for fucosylated antibodies. See Herbst, R et al. J. Pharmacol. Exp. Ther. 335(1):213-222 (2010). Thus, the Fc gamma RIV receptor is an example of a suitable Fc receptor for enrichment of afucosylated species when

TABLE 2

Exemplary full length Fc gamma RIIIb amino acid sequence

```
        10         20         30         40         50         60
MWQLLLPTAL LLLVSAGMRT EDLPKAVVFL EPQWYSVLEK DSVTLKCQGA YSPEDNSTQW 70         80         90        100        110        120
FHNESLISSQ ASSYFIDAAT VNDSGEYRCQ TNLSTLSDPV OLEVHIGWLL LQAPRWVFKE 130        140        150        160        170        180
EDPIHLRCHS WKNTALHKVT YLQNGKDRKY FHHNSDFHIP KATLKDSGSY FCRGLVGSKN 190        200        210        220        230
VSSETVNITI TQGLAVSTIS SFSPPGYQVS FCLVMVLLFA VDTGLYFSVK TNI
(SEQ ID NO: 2)
```

Examples of natural amino acid allotypes include polypeptides having the following amino acid changes in SEQ ID NO:2: S36R, S65N, A78D, N82D, I106V. Other Fc gamma RIIIb allotypes include NA1 and NA2.

Fc receptors for use in media as described herein can include an extracellular portion of an Fc gamma RIIIb polypeptide that retains the ability to bind to a glycoform of an Fc-containing polypeptide. For example, an Fc receptor can have a sequence at least 80%, 85%, 90%, 95%, 96%, 97%, 98%, 99% identical to the extracellular domain of the sequence shown in SEQ ID NO:2, or a sequence at least 80%, 85%, 90%, 95%, 96%, 97%, 98%, 99% identical to a portion thereof (e.g., a portion comprising amino acids 20-208, amino acids 20-192, amino acids 21-169, or amino acids 106-169 of SEQ ID NO:2). In various embodiments, an Fc receptor has a sequence which differs from one of these portions of an Fc gamma RIIIb sequence in at least 1 amino acid position, but not more than 15 amino acid positions (e.g., the sequence differs from amino acids 20-208 of SEQ ID NO:2 at 1, 2, 3, 4, 5, 6, 7, 8, 9, 10, 11, 12, 13, 14, or 15 amino acid positions). In various embodiments, an Fc receptor is glycosylated at a site corresponding to N180 in SEQ ID NO:2. In various embodiments, an Fc receptor lacks glycosylation at a site corresponding to N63 of SEQ ID NO:2 (e.g., due to substitution of an asparagines residue). In one embodiment, an Fc receptor comprises amino acids 20-192 of SEQ ID NO:2. In various embodiments, an Fc receptor comprises amino acids 20-192 of SEQ ID NO:2, wherein N63 is substituted for another amino acid (e.g., to glutamine, aspartic acid, or glutamic acid).

Fc gamma RIV is another Fc receptor suitable for use in some embodiments of the instant invention and is described in the review article, Nimmerjahn, F and Ravetch, J V Immunity 24:19-28 (2006). Examples of Fc gamma RIV protein sequences include those for mouse (accession number, Q8R2R4), rat (accession number, Q6XPU4), and used as an affinity ligand according to the methods of some embodiments of the instant invention.

Fc receptors for use in methods herein can be expressed in mammalian cell or other types of cells (e.g., eukaryotic cells such as yeast cells or insect cells; see exemplary host cells for production of proteins above) that produce the receptor in a form that retains an ability to bind to an Fc and to preferentially bind a glycoform. In certain embodiments, the Fc receptor is produced in prokaryotic cells, such as bacterial cells, such as E. coli. In embodiments where the Fc receptor is produced in a prokaryotic cell such as E. coli, the Fc receptor may be modified such that it retains an ability to bind to an Fc and to preferentially bind a glycoform but the Fc receptor itself is not glycosylated. Fc receptors can also be obtained from commercial sources such as R&D Systems (Minneapolis, Minn.) and Sino Biologicals, Inc. (Beijing, China). Fc receptors can be expressed and/or modified with a moiety to facilitate purification and/or coupling to a medium. In some embodiments, a receptor has a peptide tag, e.g., a polyhistidine tag or HA tag. In some embodiments, a receptor has one or more amino acid residues at a terminus to facilitate coupling. In some embodiments, a receptor has a recognition motif for an enzyme that mediates coupling, such as an LPXTG (SEQ ID NO:3) motif that is recognized by Staphylococcal Sortase A. In some embodiments, a terminus (e.g., the N-terminus) includes a lysine or cysteine. An amino acid linker that separates the terminal residue from the Fc receptor can be included. A linker can be, for example, 1-20 amino acids long, e.g., 1, 2, 3, 5, 7, 9, 10, 12, 15, or 20 amino acids long. In various embodiments, a linker includes 3, 4, or 5 adjacent glycine residues optionally followed by, or preceded by, a serine residue.

A receptor may include at its N-terminus a KGGG (SEQ ID NO:4) or CGGG (SEQ ID NO:5) motif.

In one example, an Fc receptor includes the following amino acid sequence:

```
                                                            (SEQ ID NO: 6)
         KGGGEDLPKAVVFLEPQWYRVLEKDSVTLKCQGAYSPEDNSTQWFHNESLISSQASS

YFIDAATVDDSGEYRCQTNLSTLSDPVQLEVHIGWLLLQAPRWVFKEEDPIHLRCHSWKNTALHKVT

YLQNGKGRKYFHHNSDFYIPKATLKDSGSYFCRGLVGSKNVSSETVNITITQGLAVSTISSFFPPGY

QV.
```

In another example, an Fc receptor includes the following amino acid sequence:

```
                                                            (SEQ ID NO: 7)
CGGGEDLPKAVVFLEPQWYRVLEKDSVTLKCQGAYSPEDNSTQWFHNESLISSQASSYFIDAATVDD

SGEYRCQTNLSTLSDPVQLEVHIGWLLLQAPRWVFKEEDPIHLRCHSWKNTALHKVTYLQNGKGRKY

FHHNSDFYIPKATLKDSGSYFCRGLVGSKNVSSETVNITITQGLAVSTISSFFPPGYQV.
```

Methods and compositions of the present disclosure encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to the sequence specified are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%. 91%, 92%, 93%, 94%, 95%, 96%, 97%, 98% or 99% identity to the sequence specified are termed substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol Biol.* 48:444-453) algorithm which has been incorporated into the GAP program in the GCG software package (available at http://www(dot)gcg(dot)com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www(dot)gcg(dot)com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to nucleic acid molecules of some embodiments of the invention. BLAST protein searches can be performed with the XBLAST program, score=50, wordlength=3 to obtain amino acid sequences homologous to protein molecules of some embodiments of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Nucleic acid molecules corresponding to natural allelic variants, homologs, orthologs, or other related sequences (e.g., paralogs) of the sequences described herein can be isolated based on their homology to the nucleic acids encoding the amino acid sequences disclosed herein, for example by performing standard or stringent hybridization reactions using all or a portion of the known sequences as probes. Such methods for nucleic acid hybridization and cloning are well known in the art.

The homologs of the peptides as provided herein typically have structural similarity with such peptides. A homolog of a polypeptide includes one or more conservative amino acid substitutions, which may be selected from the same or different members of the class to which the amino acid belongs.

In one embodiment, the sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Some embodiments of the present invention also encompass conservative substitution (substitution and replacement are both used herein to mean the interchange of an existing amino acid residue with an alternative residue) that may occur e.g., like-for-like substitution such as basic for basic, acidic for acidic, polar for polar, etc. Non-conservative substitution may also occur e.g., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as 0), pyridylalanine, thienylalanine, naphthylalanine and phenylglycine. Conservative substitutions that may be made are, for example, within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxylamino acids (Serine, Threonine), large amino acids (Phenylalanine and Tryptophan) and small amino acids (Glycine, Alanine).

Producing Fc Receptor Media

Fc receptors can be coupled to a medium (e.g., a solid support) by any of a variety of techniques. In some embodiments, a receptor is coupled to a medium by one or more covalent bonds, e.g., formed by reaction of functional groups on the receptor or the medium. Examples of functional groups include hydroxyl groups, amine groups, thiol groups, thiopropyl groups, carbonyl groups, N-hydroxysuccinimide (NHS) esters, epoxides (e.g., epichlorohydrin), carbonyldiimidazole (CU) activated esters, cyanogens (cyanogens bromide (CNBr)), N,N-disuccinimidylcarbonate (DSC), or aldehydes. In some embodiments, an Fc receptor is coupled via a disulfide bond. In some embodiments, an Fc receptor is coupled to a medium using metal chelation. In some embodiments, an Fc receptor is coupled using a histidine tag. Other compounds useful for coupling include tosyl chloride, tresyl chloride, ECH linkage (e.g., using ECH-Lysine Sepharose 4 Fast Flow, GE Healthcare) or EAH linkage (e.g., using EAH-Sepharose® 4B, GE Healthcare). In certain embodiments, an Fc receptor is coupled via its C-terminus to a medium (e.g., a solid support). In certain embodiments, an Fc receptor is coupled via its N-terminus to a medium (e.g., a solid support).

A receptor can be directly coupled to a medium or indirectly coupled via a linker. Any of a variety of linkers are suitable for coupling a medium to a receptor. In some embodiments, a linker includes a chain of carbon, oxygen and nitrogen atoms, e.g., a linear, branched, or cyclic chain, e.g., a chain having 1-30 carbon atoms.

Methods of coupling polypeptides to media are described, e.g., in WO 90/09237; Hermanson et al., Immobilized Affinity Ligand Techniques, Academic Press, 1992; U.S. Pat. Nos. 5,260,373; 5,874,165; 3,932,557; 4,772,635; 4,210,723; 5,250,613; 5,543,054; 6,399,750; EP 1352957 A1, and WO 2004/074471.

In some embodiments, a receptor is coupled to a medium comprising agarose having a functional group, such as CNBr or NHS, and optionally, a linker. In some embodiments, a receptor is coupled via primary amino groups to NHS-activated Sepharose® 4 Fast Flow. In one exemplary method, a receptor is coupled by washing the NHS-activated Sepharose® 4 Fast Flow medium with 1 mM HCl, mixing the medium with the receptor, allowing coupling to occur (e.g., by incubation at room temperature for 1-4 hours), washing the medium with 100 mM Tris to quench non-reacted groups.

Enzyme-mediated coupling can be used to link a receptor to a medium (see, e.g., Chan et al., PLoS ONE 2(11):e1164, 2007). For example, a receptor can be designed to include a recognition motif for a transpeptidase such as Staphylococcal Sortase A. Recognition and cleavage at an LPXTG (SEQ ID NO: 3) motif by Sortase A generates an acyl-enzyme intermediate that is reactive with an available glycine or aminomethylene. If a receptor having a recognition motif is cleaved by Sortase A, it becomes linked to a medium having reactive sites. In one example, beads modified to include one, two, three, or four glycine residues are linked to receptors having a C-terminal LPXTG (SEQ ID NO: 3) motif by Sortase A-mediated ligation.

Suitable types of media include beads, membranes, matrices, porous media, gels, plates, columns, and monoliths. A medium can be comprised of a material such as agarose, cellulose, or dextran, ceramic, metal, glass, nylon, TEFLON® (polytetrafluoroethylene), nylon, polycarbonate, polyacrylamide, polystyrene, polypropylene, polyether sulfone, polyamide, polytetrafluoroethylene, polysulfone, polyester, polyvinylidene fluoride, a fluorocarbon, e.g. poly(tetrafluoroethylene-co-perfluoro(alkyl vinyl ether)), polyethylene, polyacrylate, or poly(azolactone).

An Fc receptor medium is coupled to a concentration of Fc receptor that is sufficient for binding to an Fc-containing polypeptide. In some embodiments, a medium has 0.01-15 mg/ml of an Fc receptor (e.g., 0.1-15 mg/ml, or 1-15 mg/ml). In some embodiments, a medium has between 2-10 mg/ml (e.g., between 3-7.5 mg/ml) of an Fc receptor.

Separation Methods

To separate polypeptide glycoforms, a load fluid is contacted with an Fc receptor medium as described herein under conditions in which polypeptide binds to the medium. The medium is optionally washed, and is contacted with a solution that elutes polypeptide that bound to the medium. In some embodiments, polypeptide that elutes from the medium is recovered. In some embodiments, polypeptide that flows through the medium (e.g., polypeptide that is not bound by the medium) is recovered.

A load fluid can be, for example, a cell culture medium containing a polypeptide of interest (e.g., medium comprising cells, or medium from which cells are removed), a cell extract, serum, ascites, a purified or partially purified preparation from cell culture, extract, serum, etc., or a formulated drug product or drug substance. In a particular embodiment, the load fluid comprises serum IgG. In some embodiments, a load fluid is an eluate of a protein A column. A load fluid may contain a polypeptide at a concentration between 0.001-500 mg/mL (e.g., 0.001-100 mg/ml, 0.001-30 mg/ml, 0.001-10 mg/ml). A polypeptide can be contacted with a medium at a concentration of 0.1 mg polypeptide per 25,000 ml of medium.

Before contacting a medium with a load fluid, parameters such as pH, ionic strength, and temperature may be adjusted if necessary. A medium may be equilibrated by washing it with a solution (e.g., a buffer for adjusting pH, ionic strength, etc., or for the introduction of a detergent) to bring characteristics that allow or facilitate binding and/or separation of a polypeptide.

In some embodiments, an Fc receptor medium is flushed and equilibrated with one or more solutions prior to contact with a polypeptide. Such solutions can include, for example, a buffer (e.g., Tris, MES, HEPES, histidine, or phosphate, e.g., between 1-500 mM, 25-100 mM, or 50 mM), and/or salt (e.g., NaCl, $NaPO_4$, sodium acetate, or $CaCl_2$, e.g., between 0-2M, or 5-250 mM). The pH of an equilibration solution is generally between 3.5-10 (e.g., between pH 6.0-8.0). In some embodiments, an equilibration buffer contains 10 mM to about 50 mM of Tris or MES and 10-200 mM of a salt (e.g., 150 mM NaCl or 20 mM $CaCl_2$).

After contacting an Fc receptor medium with a load fluid, the bound medium can be washed. Wash solutions can include a buffer (e.g., Tris, MES, HEPES, phosphate, or histidine, e.g., between 1 and 500 mM), and/or salt (e.g., NaCl, $CaCl_2$, $NaPO_4$, or sodium acetate, e.g., between 0 and 2 M), and/or an additive (e.g. guanidine, urea, sucrose, arginine, or an arginine derivative), and/or a solvent (e.g., ethanol, acetonitrile, or polyethylene glycol). Wash solutions generally have a pH between 3.5 and 10 (e.g., a pH between 4.5-8.0).

In some embodiments, a medium is washed with the same solution as used to equilibrate the medium. In some embodiments, a medium is washed with 1 mM HEPES.

Polypeptides can be eluted from an Fc receptor medium using a step or gradient change in pH, salt type, salt concentration, solvent type, solvent concentration, displacer type, displacer concentration, or a combination thereof. Proteins containing Fc regions, other proteins, small polypeptides with homology to Fc regions, detergents, hydrophobic solutes, polyelectrolytes, amino acids, antibiotics, sugars, dextrans, ficolls, dendritic polymers etc could be used as displacers. In general, to elute a polypeptide from an Fc receptor medium, the medium is contacted with an elution buffer. In some embodiments, an elution buffer contains of a salt (e.g., NaCl or $CaCl_2$, e.g., 0-2M, e.g., 10-100 mM). In some embodiments, an elution buffer may contain glycine, acetic acid, or citric acid (e.g., 20 mM-250 mM, e.g., 150 mM). An elution buffer may also contain a buffer (e.g., HEPES, e.g., 10-100 mM). An elution buffer may also contain acetic acid (e.g., 20 mM to about 50 mM), an additive (e.g. guanidine, urea, or sucrose), and/or a solvent (e.g., ethanol, acetonitrile, polyethylene glycol, e.g., 1-10% solvent, e.g., 5% solvent). The pH of the elution buffer may range from about 2.0 to about 4.0. In some embodiments, pH can be changed (e.g., gradually) to produce a gradient elution (e.g., a gradient elution from pH 5.0 to pH 3.0). In one embodiment, the pH of the elution buffer is about 3.0. An eluate can be neutralized, e.g., by adjusting pH to 6.0-8.0 (in cases in which low pH is used for elution) after recovery from the medium.

A medium may optionally be cleaned, i.e., stripped and regenerated, after elution of a polypeptide. This can be performed regularly to minimize the building up of impurities on the surface of the solid phase and/or to sterilize the matrix to avoid contamination of the product with microorganisms.

Solution components may be adjusted according to the knowledge of the person of ordinary skill in the art. Sample solution composition ranges are provided in the Examples below. Not all of the solutions or steps are necessary, but are provided for illustration.

A separation using an Fc receptor medium may be performed alone or in combination with other techniques. In some embodiments, one or more processes are used to prepare load fluid, e.g., to reduce the load challenge of contaminants or impurities. In some embodiments, one or more processes are used to process an eluate or flow-through of an Fc receptor medium.

Purification/separation techniques that can be practiced in combination with Fc receptor methods described herein include depth filtration, diafiltration, ultrafiltration, viral removal filtration, protein A chromatography, protein G chromatography, cation exchange chromatography, anion exchange chromatography, size exclusion chromatography, hydrophobic interaction chromatography, immobilized metal affinity chromatography, hydroxyapatite chromatography, lectin chromatography, biomimetic affinity chromatography, mixed mode chromatography, and combinations thereof. Techniques herein can be practiced in column, membrane, and/or expanded bed adsorption formats. In certain embodiments, one or more chromatographic techniques are operated in a weak partitioning mode (see U.S. Pub. No. 2007/0060741 and Kelley B D, Tobler S A, Brown P, Coffman J L, Godavarti R, Iskra T, Switzer M, Vunnum S. *Biotechnol Bioeng.* 2008 Oct. 15; 101(3): 553-66).

Commercially available protein A chromatography columns include, for example, PROSEP-A™ (Millipore, U.K.), Protein A Sepharose FAST FLOW™ (GE Healthcare, Piscataway, N.J.), TOYOPEARL™ 650M Protein A (TosoHass Co., Philadelphia, Pa.), and MabSelect™ columns (GE Healthcare, Piscataway, N.J.).

Anionic exchange resins that can be used include resins having substituents such as diethylaminoethyl (DEAE), trimethyalaminoethyl (TMAE), quaternary aminoethyl (QAE) and quaternary amine (O) groups.

Cationic exchange resins that can be used include resins having substituents such as carboxymethyl (CM), sulfoethyl (SE), sulfopropyl (SP), phosphate (P) and sulfonate (S).

In some embodiments, a cellulosic ion exchange resin (e.g., DE23, DE32, DE52, CM-23, CM-32 or CM-52, available from Whatman Ltd. Maidstone, Kent, U.K) is used. Sephadex-based and cross-linked ion exchangers used for purification include, for example, DEAE-, QAE-, CM-, and SP-Sephadex, and DEAE-, Q-, CM- and S-Sepharose, and Sepharose (Amersham Biosciences, Piscataway, N.J.). DEAE and CM derivatized ethylene glycol-methacrylate copolymer such as TOYOPEARL™ DEAE-650S or M and TOYOPEARL™ CM-650S or M are available from Toso Haas Co., Philadelphia, Pa.

In some embodiments, a hydrophobic interaction chromatography (HIC) resin is used for purification. HIC separates molecules based on hydrophobicity. Generally, sample molecules in a high salt buffer are loaded onto the HIC resin. Salt in the buffer interacts with water molecules to reduce the solution of the molecules in solution, thereby exposing hydrophobic regions in the sample molecules which are consequently absorbed by the HIC medium. The more hydrophobic the molecule, the less salt needed to promote binding. Binding interactions between the product molecules and a HIC medium thus depend on conditions such as pH, ionic strength, and salt concentrations of the medium. Commercially available HIC resins that can be used include resins comprising a base matrix (e.g., cross-linked agarose or synthetic copolymer material) to which hydrophobic ligands (e.g., alkyl or aryl groups) are coupled. Examples include PhenylSEPHAROSE™, 6 FAST FLO™ (Pharmacia LKB Biotechnology, AB, Sweden); Phenyl SEPHAROSE™ High Performance (Pharmacia LKB Biotechnology, AB, Sweden); Octyl SEPHAROSE™ High Performance (Pharmacia LKB Biotechnology, AB, Sweden); Fractogel™ EMD Propyl or FRACTOGEL™ EMD Phenyl (E. Merck, Germany); MACRO-PREP™ Methyl or MACRO-PREP™ t-Butyl Supports (Bio-Rad, CA); WP HI-Propyl ($C_3$)™ (J. T. Baker, N.J.); and TOYOPEARL™ ether, phenyl or butyl (TosoHaas, Pa.). HIC can be performed in a weak partitioning mode.

In some embodiments hydroxyapatite chromatography is used for purification. Hydroxyapatite chromatography utilizes an insoluble hydroxylated calcium phosphate of the formula $[Ca_{10}(PO_4)_6(OH)_2]$, as both the matrix and the ligand. Functional groups consist of pairs of positively charged calcium ions (C-sites) and clusters of negatively charged phosphate groups (P-sites). Binding interactions between a product and a hydroxyapatite medium depend on conditions such as the pH, ionic strength, and excipient concentrations, such as phosphate concentrations, calcium concentrations, arginine concentrations, glycine concentrations, and HEPES concentrations of the medium. Various hydroxyapatite chromatographic resins are available commercially. Hydroxyapatite chromatography can be performed in a weak partitioning mode.

In some embodiments, an immobilized metal affinity chromatography (IMAC) resin is used for purification. IMAC is based on the interaction between chelated transition metal ions immobilized on a resin and imidazole side chains of histidine residues on a tagged product of interest. Separation of molecules occurs as a result of competition between the tagged product of interest and counterligands for metal groups on the IMAC resin. Binding interactions between a product and metal-charged IMAC medium depend on conditions such as counterligand levels, such as imidazole concentrations, and ionic strength of the medium. Various IMAC resins are available commercially. IMAC can be performed in a weak partitioning mode.

In some embodiments, lectin chromatography is used for purification (see, e.g., Tojo et al., Biol. Pharm. Bull. 32(9): 1604-1608, 2009; and Shinkawa et al., supra).

Characterization of Polypeptides

Polypeptides separated using Fc receptor media described herein can be analyzed for any type of characteristic, such as glycan quantity and/or structure, stability (e.g., half life, shelf life), toxicity, and biological activity. Polypeptides in any stage of a separation process, e.g., eluates and/or flow through portions, may be analyzed. Evaluation of glycoforms may be, for example, by way of comparison of load fluid and eluate, or by way of comparison of load fluid and flow through, or by way of comparison of eluate to a reference sample.

Any available technique for detecting and characterizing glycans can be applied. For example, glycan structure can be analyzed by mass spectrometry (MS), chromatographic methods, electrophoretic methods, nuclear magnetic resonance (NMR), and combinations thereof. Chromatographic methods can include high performance liquid chromatography, liquid chromatography, ultra performance liquid chromatography, thin layer chromatography, and/or amide column chromatography. MS can include tandem MS, LC-MS, LC-MS/MS, matrix assisted laser desorption ionization MS (MALDI-MS), and/or electron transfer dissociation MS (ETD-MS). Electrophoretic methods can include capillary electrophoresis, gel electrophoresis (e.g., with or without Western blotting to detect glycan and/or polypeptide structures). NMR can include 1D-NMR, 2D-NMR, correlation spectroscopy NMR, heteronuclear single quantum coherence NMR, heteronuclear multiple quantum coherence NMR, rotational nuclear overhauser effect spectroscopy NMR, and/or nuclear overhauser effect spectroscopy NMR.

Various techniques for analyzing glycans have been described. See, e.g., Bigge et al. (Anal. Biochem. 230:229-238, 1995), which describes conditions for labelling fucosylated and afucosylated glycans with 2-amino benzamide (2-AB) and 2-anthranilic acid (2-AA) for detection by chromatographic and mass spectrophotometric means. See also Anamula et al., Anal. Biochem. 350(1):1-23, 2006; Townsend, R. R. Carbohydrate Analysis" High Performance Liquid Chromatography and Capillary Electrophoresis., Ed. Z. El Rassi, pp 181-209, 1995; and Ruhaak et al., Anal Bioanal Chem. 397(8):3457-81, 2010.

Polypeptides expressed in cells exhibit heterogeneous glycosylation. Molecules of a given polypeptide may vary in the number and type of a given sugar residue. The present disclosure provides media and methods for separating glycoforms, e.g., to enrich for polypeptides having increased or decreased levels of particular residues. In some embodiments, a glycoform has "reduced" levels of a particular sugar (e.g., fucose), if the number of fucose residues are fewer than the number of residues on a reference glycoform. In some embodiments, a reference glycoform is a glycoform having an average or maximal number of residues of the particular sugar observed on the polypeptide expressed in a given cell type. For example, if an antibody polypeptide expressed in a CHO cell has a maximum of two core fucose residues, a glycoform having 0 or 1 core fucose has "reduced" levels.

Likewise, a glycoform has "increased" levels of a particular sugar if the number of sugars are higher than the number of residues on a reference glycoform. In some embodiments, a reference glycoform is a glycoform having an average or minimal number of residues of the particular sugar.

Detection of glycoforms for evaluation of separation can be performed by any available means, and can involve analysis glycans of any of load fluid, eluate, flow through, washes, or combinations thereof.

In some embodiments, the percentage of a glycoform in an eluate or flow through of an Fc receptor medium is altered (e.g., increased or decreased) by at least 20%, 50%, 100%, 2 fold, 5 fold, 10 fold, 20 fold, 50 fold, or 100 fold, relative to the load fluid. In some embodiments, the proportion of a glycoform in an eluate or flow through of an Fc receptor medium is increased to at least 10%, 20%, 30%, 40%, 50%, 60%, 70%, 80%, 90%, 95%, or 99% of the total. For example, in some embodiments, separation of a recombinant antibody sample using an Fc gamma RIII receptor medium described herein results in an eluate having at least 40% afucosylated material, whereas a sample that has not been subjected to separation (e.g., load fluid) may typically have 5-7% afucosylated material (depending on the cell system for expression and other factors).

Binding of polypeptides separated according to methods provided herein can be analyzed. In some embodiments, binding to a target protein (e.g., antibody binding to antigen) is analyzed. In some embodiments, binding to an Fc receptor is analyzed. Methods for evaluating binding interactions are known and include, for example, ELISA, BIACore™ biosensor analysis, fluorescent resonance energy transfer (FRET), and others.

Any available method for evaluating a biological activity of a polypeptide may be employed. In some embodiments, a glycoform-specific biological activity is evaluated. ADCC can be analyzed by known methods (see, e.g., Shinkawa et al., supra). Changes in relative proportion of one or more polypeptide glycoforms as a result of separation using a medium herein may result in a change in a biological activity, such as an increase in ADCC, e.g., by at least 20%, 50%, 100%, 2 fold, 5 fold, 10 fold, 20 fold, 50 fold, or 100 fold, relative to activity of polypeptides in a load fluid or a reference sample.

Products and Uses

Methods and compositions herein for separation of polypeptides have numerous applications. Methods permit preparation of polypeptides having a desired glycoform profile. In some embodiments, methods are used to enrich for a glycoform of interest (e.g., a glycoform having an enhanced biological activity). In some embodiments, methods are used to normalize glycoform profiles (e.g., between batches, or between molecules produced by different processes). In some embodiments, methods are used to provide glycoform pools that can be evaluated for any desired characteristic, such as biological activity. The ability to control glycoform profiles allows greater control and flexibility in manufacturing processes. The present technology is an additional tool for achieving batch-to-batch consistency for a given product. It is also useful, e.g., for the comparison of products made by different processes and/or different manufacturers. Furthermore, a manufacturer can use the technology to match a quality attribute of another manufacturer's product, e.g., in the development of a biosimilar product, or to alter (e.g., increase or enhance) a quality attribute in a follow-on product.

The present disclosure also relates to a product prepared according to a method described herein. In some cases, it will be desirable to further isolate and/or purify polypeptides isolated according to the present disclosure and formulate them for pharmaceutical use according to standard methods. See for example *Protein Purification Principles and Practice* 2nd Edition, Springer-Verlag, New York, 1987; Higgins, S. J. and Hames, B. D. (eds.), and Deutscher, M. P., Simon, M. I., Abelson, J. N. (eds.), *Guide to Protein Purification: Methods in Enzymology* (Methods in Enzymology Series, Vol 182), Academic Press, 1997, incorporated herein by reference. One of ordinary skill in the art will appreciate that the exact techniques used will vary depending on the character of the polypeptide. Polypeptides having pharmacologic activity will be useful in the preparation of pharmaceuticals. These may be administered to a subject or may first be formulated for delivery by any available route including, but not limited to parenteral (e.g., intravenous), intradermal, subcutaneous, oral, nasal, bronchial, opthalmic, transdermal (topical), transmucosal, rectal, and vaginal.

A pharmaceutical composition of the product is formulated to be compatible with its intended route of administration according to methods known in the art, see for example, Remington: *The Science & Practice of Pharmacy*, 19th ed., Williams & Williams, (1995), and the *Physician's Desk Reference*, 52nd ed., Medical Economics, Montvale, N.J. (1998). In some embodiments, the product is formulated using sterile water (e.g., SWFI), buffered saline (e.g., phosphate buffered saline), polyol (e.g., glycerol, propylene glycol, liquid polyethylene glycol), or suitable mixtures thereof.

EXEMPLIFICATION

Example 1

This example describes preparation of an Fc gamma RIIIa receptor medium and use of the medium with mAb1, a humanized IgG1 monoclonal antibody produced in CHO cells.

An extracellular domain of an Fc-gammaRIIIa-176V (valine) allotype receptor having the following amino acid sequence was transiently expressed in HEK-293 cells:

(SEQ ID NO: 8)
EDLPKAVVFLEPQWYRVLEKDSVTLKCQGAYSPEDNSTQWFHNESLISSQASSYFIDAATVDDSGEY

RCQTNLSTLSDPVQLEVHIGWLLLQAPRWVFKEEDPIHLRCHSWKNTALHKVTYLQNGKGRKYFHHN

SDFYIPKATLKDSGSYFCRGLVGSKNVSSETVNITITQGLAVSTISSFFPPGYQVHHHHHHHHHH

The receptor was expressed with a signal peptide that was cleaved during cellular processing. A 10-his tag (SEQ ID NO: 15) was expressed at the C-terminus for purification, which was performed using a nickel affinity column.

The Fc-gamma receptor (1.25 ml in PBS at 0.85 mg/ml) was added to 0.73 ml of activated NHS Sepharose™ 4 Fast Flow resin (17-0906-01, GE) and allowed to react for 80 minutes at room temperature. The reaction was quenched with 100 mM TRIS pH 8.3. The coupling efficiency, determined using size exclusion chromatography, was 100%. The resin was packed to 0.63 mL in a 0.5 cm internal diameter (ID) column (GE Healthcare) and flushed with 10 mls of 100 mM Tris pH 8.3 followed by 10 mls of 100 mM Acetate pH 4.0 with 500 mM NaCl. This flushing was repeated twice and the column was stored in 16% ethanol, 150 mM NaCl 50 mM Tris pH 7.7.

The column was flushed with 50 mM Tris 150 mM NaCl pH 7.2 and loaded at 0.25 ml/min (2.5 min residence time) with 50 ml of 0.34 mg/ml mAb1 in PBS buffer (27.0 mg protein/ml resin). The mAb1 material was prepared with a two column purification process in which a protein A chromatography column and an anion exchange chromatography column were used. After the mAb1 material was loaded on the Fc receptor column, the column was flushed with 12 ml of PBS at 0.5 ml/min and eluted with 50 mM HEPES pH 3.0 at 0.5 ml/min. mAb1 was collected (0.1 mg in 7.5 ml), as determined by absorbance at 280 nm and size exclusion chromatography.

To facilitate glycan analysis, the eluted mAb1 sample was concentrated to 0.45 mg/ml in 115 microliters using 16.5 microliters of Protein A resin (GE MabSelect, 17-5199-03). The Protein A concentration was performed in batch mode using a 96 well plate, a PBS wash buffer, a 150 mM glycine elution buffer (pH3.0), and a MES neutralization buffer (pH 6.8).

To determine the percentage of non-fucosylated mAb1, approximately 35 μg was digested with PNGase F at 37° C. for 16 hours to release Fc-oligosaccharides. The released N-linked oligosaccharides were labeled with 2-amino benzamide (2-AB) for 3 hours at 65° C. Residual 2-AB was removed using acetone precipitation. Oligosaccharide analysis was performed using an Xbridge Amide HILIC-HPLC at 45° C. over a linear ammonium formate gradient with fluorescence detection.

The starting mAb1 material had 7% non-fucosylated Fc. After enrichment using the Fc receptor column, the mAb1 material had 61% non-fucosylated IgG Fc. FIG. 1 shows an example of the typical oligosaccharide profile of mAb1 (top panel) and the profile of mAb1 after enrichment using the Fc receptor column (bottom panel). All peaks that have labels ending in 'F' are fucosylated and all peaks have labels that do not end in 'F' in FIG. 1 are afucosylated.

Example 2

The packed Fc receptor column described in Example 1 was used to enrich the non-fucosylated glycoform of a second monoclonal antibody, mAb2, which is a humanized IgG1 produced in CHO cells. The mAb2 material was obtained from a ultrafiltration pool that results from a purification process using the following: a protein A chromatography column, an anion exchange chromatography column, a virus-retaining filter (e.g., a Planova 20 filter (Asahi Kasei Corporation, Tokyo, Japan)), and an ultrafilter.

The Fc receptor column was flushed with equilibration buffer (50 mM MES with 20 mM $CaCl_2$ at pH 6.5) and loaded at 0.25 ml/min (2.5 min residence time) with 50 ml of 1.80 mg/ml mAb2 in equilibration buffer (142.9 mg protein/ml resin). The column was then flushed with 12 ml of equilibration buffer at 0.5 ml/min and eluted with 150 mM Glycine at pH 3.4 at 0.5 ml/min. mAb2 was collected (0.12 mg in 9.25 ml), as determined by absorbance at 280 nm. The peak was brought to pH 6.6 with pH 6.8 1 M MES neutralization buffer. To facilitate glycan analysis, the mAb2 sample was concentrated to 0.87 mg/ml in 100 microliters using an Amicon Ultra-4 10,000 kD MWCO device (Millipore UFC801024).

The percentage of non-fucosylated mAb2 was determined using the method described in Example 1. The starting mAb2 material had about 5% non-fucosylated Fc. After enrichment using the Fc receptor column, the mAb2 material had 48.7% non-fucosylated IgG Fc.

A similar procedure as above was used to enrich a significant amount of mAb2 using multiple cycles and running at a lower load challenge to minimize process time and material waste. The column was flushed with equilibration buffer (PBS) and loaded at 0.25 ml/min (2.5 min residence time) with 1 ml of 1.89 mg/ml mAb2 in equilibration buffer (3.0 mg protein/ml resin). The column was then flushed with 12 ml of equilibration buffer at 0.5 ml/min and eluted with 150 mM Glycine at pH 3.4 at 0.5 ml/min. This procedure was repeated 39 times for a total of 40 cycles. The total peak was brought to approximately pH 6.5 using 15% v/v pH 10.4 1 M MES neutralization buffer. A total of 4.4 mg of mAb2 was collected, as determined by absorbance at 280 nm. To facilitate glycan analysis, the mAb2 sample was concentrated to 2.3 mg/ml in 1.9 ml using an Amicon Ultra-4 10,000 kD MWCO device (Millipore UFC801024).

The percentage of non-fucosylated mAb2 was determined using the method described in Example 1. The starting mAb2 material had 5.9% non-fucosylated and 2.3% mannosylated IgG Fc. After enrichment using the Fc receptor column, the mAb2 material that bound to the media had 41.8% non-fucosylated and 6.3% mannosylated IgG Fc. The mAb2 material that flowed through the column had 4.3% non-fucosylated and 2.0% mannosylated IgG Fc.

Example 3

A column packed with an Fc receptor medium was prepared as described in Example 1. This medium was used to analyze binding interactions between the Fc receptor and an Fc fusion protein having a triple mutation, L234A, L235A, and G237A, which is known to known to prevent induction of antibody dependent cellular cytotoxicity (ADCC) (The 234, 235, 237 amino acid positions are according to the Kabat numbering system). The Fc fusion protein material was obtained from a three column purification process using the following: aprotein A chromatography column, an anion exchange chromatography column and a mixed mode chromatography column with cationic and HIC character.

The Fc receptor column was flushed with 50 mM MES 150 mM NaCl pH 6.5 and loaded at 0.25 ml/min (3.0 min residence time) with 5 ml of 2.0 mg/ml Fc fusion in 50 mM MES 150 mM NaCl pH 6.5 (15.6 mg protein/ml resin). The column was then flushed with 9 ml of 50 mM MES 150 mM NaCl pH 6.5 at 1 ml/min and eluted with 12 ml of 150 mM Glycine pH 3.0 at 1 ml/min. The peak was neutralized with a 15% spike of 1 M MES pH 10.4. This procedure was repeated with mAb2, which does not have a corresponding triple mutation, followed by the triple mutant Fc fusion protein again. Comparison of the chromatograms measured by absorbance at 280 nm clearly showed that the Fc fusion material in the low pH elutions did not produce a significant peak relative to the non-mutated mAb2. Therefore the triple mutant protein does not significantly bind to Fc gamma RIIIA.

Example 4

This example describes preparation of an Fc gamma RIIa receptor medium and use of the medium with mAb2.

Fc gamma RIIa receptors bind to IgG1 and other IgG subclasses. An extracellular domain of an Fc gamma RIIa receptor was obtained from R&D Systems, (Minneapolis, Minn.). The receptor was expressed in NSO (murine myeloma)-derived cells and contains a 10-his tag (SEQ ID NO: 15) was expressed at the C-terminus. The portion of the Fc gamma RIIa receptor has the following amino acid sequence (see also GenBank Accession # AAA35827):

```
                                                        (SEQ ID NO: 9)
AAPPK AVLKLEPPWI NVLQEDSVTL TCQGARSPES DSIQWFHNGN LIPTHTQPSY

RFKANNNDSG EYTCQTGQTS LSDPVHLTVL SEWLVLQTPH LEFQEGETIM LRCHSWKDKP

LVKVTFFQNG KSQKFSHLDP TFSIPQANHS HSGDYHCTGN IGYTLFSSKP VTITVQVPSM

GSSSPMGI.
```

The receptor was expressed with an N-terminal signal peptide that is removed and the remaining portion of the molecule is the extracellular domain (Ala 36 to Ile 218).

Fc gamma receptor (1.23 ml in PBS at 0.82 mg/ml) was added to 0.82 ml of activated NHS Sepharose 4 Fast Flow resin (17-0906-01, GE Healthcare) and allowed to react for 60 minutes at room temperature. The reaction was quenched with 100 mM TRIS pH 8.5. The coupling efficiency, determined using size exclusion chromatography, was 94%. The resin was packed to 0.72 mL in a 0.5 cm ID column (GE Healthcare) and flushed with 10 mls of 100 mM Tris pH 8.5 followed by 10 mls of 100 mM Acetate pH 4.0 with 500 mM NaCl. This was repeated twice and the column was stored in 16% ethanol, 150 mM NaCl 50 mM Tris pH 7.7.

The column was flushed with PBS and loaded at 0.25 ml/min (2.9 min residence time) with 5 ml of 2.0 mg/ml mAb2 in PBS buffer (13.9 mg protein/ml resin). The column was then flushed with 9 ml of PBS at 1 ml/min and eluted with 12 ml of 150 mM Glycine pH 2.6 at 1 ml/min. The peak was neutralized with a 15% spike of 1 M MES pH 10.4. This procedure was repeated nine times and the ten peaks were pooled to produce 95.4 ug of mAb2 as determined by absorbance at 280 nm and size exclusion chromatography. To facilitate glycan analysis, the mAb2 sample was concentrated to 0.51 mg/ml in 150 microliters using a 30 kD MWCO ultracentrifuge membrane.

To determine the glycan profile of mAb2, approximately 35 μg was digested with PNGase F at 37° C. for 16 hours to release Fc-oligosaccharides. The released N-linked oligosaccharides were labeled with 2-AB for 3 hours at 65° C. Residual 2-AB was removed using acetone precipitation. The oligosaccharide analysis was done on a Xbridge Amide HILIC-HPLC at 45° C. over a linear ammonium formate gradient with fluoresence detection. There was no alteration in the proportion of fucosylated glycoforms in the sample compared to that of the load material. Both the load and the eluted peak had about 5% fucosylated material.

Example 5

This example describes preparation of an Fc gamma RIIb/c receptor medium and use of the medium with mAb2.

Fc gamma RIIB/C receptors bind to IgG1 and other IgG subclasses. An extracellular domain of an Fc gamma RIIb/c receptor from R&D Systems (Minneapolis, Minn.) was obtained. The receptor was expressed in NSO-derived cells and contained a C-terminal 10-his tag (SEQ ID NO: 15), and has the following amino acid sequence (see also GenBank Accession # P31994):

The receptor was expressed with a signal peptide that is cleaved off the N terminus, and the remaining portion of the molecule is the extracellular domain (Ala46 to Pro 217).

Fc gamma receptor (0.87 ml in PBS at 1.16 mg/ml) was added to 0.82 ml of activated NHS Sepharose 4 Fast Flow resin (17-0906-01, GE) and allowed to react for 60 minutes at room temperature. The reaction was quenched with 100 mM TRIS pH 8.5. The coupling efficiency, determined using size exclusion chromatography, was 95%. The resin was packed to 0.72 mL in a 0.5 cm ID column (GE Healthcare) and flushed with 10 mls of 100 mM Tris pH 8.5 followed by 10 mls of 100 mM Acetate pH 4.0 with 500 mM NaCl. This was repeated twice and the column was stored in 16% ethanol, 150 mM NaCl 50 mM Tris pH 7.7.

The column was flushed with PBS and loaded at 0.25 ml/min (2.9 min residence time) with 5 ml of 2.0 mg/ml mAb2 in PBS buffer (13.9 mg protein/ml resin). The column was then flushed with 9 ml of PBS at 1 ml/min and eluted with 12 ml 150 mM Glycine pH 2.3 at 1 ml/min. The peak was neutralized with a 15% spike of 1 M MES pH 10.4. This procedure was repeated nine times and the ten peaks were pooled to produce 93.0 ug of mAb2 as determined by absorbance at 280 nm and size exclusion chromatography. To allow glycan analysis, the mAb2 sample was concentrated to 0.74 mg/ml in 100 microliters using a 30 kD MWCO ultracentrifuge membrane.

To determine the glycan profile of mAb2, approximately 35 μg was digested with PNGase F at 37° C. for 16 hours to release Fc-oligosaccharides. The released N-linked oligosaccharides were labeled with 2-AB for 3 hours at 65° C. Residual 2-AB was removed using acetone precipitation. The oligosaccharide analysis was done on a Xbridge Amide HILIC-HPLC at 45° C. over a linear ammonium formate gradient with fluoresence detection. There was no alteration in the proportion of fucosylated glycoforms in the sample compared to that of the load material. Both the load and the eluted peak had about 5% fucosylated material.

Example 6

This example describes preparation of an Fc gamma RI receptor medium and use of the medium with mAb2.

Fc gamma RI receptors bind to IgG1 and other IgG subclasses. An extracellular domain of an Fc gamma RI receptor was obtain from R&D Systems (Minneapolis, Minn.). This receptor, which was expressed in NSO-derived cells and contained a C-terminal 6-his tag (SEQ ID NO: 16), has the following amino acid sequence (see also GenBank Acc. # P12314):

```
                                                        (SEQ ID NO: 10)
APPKA VLKLEPQWIN VLQEDSVTLT CRGTHSPESD SIQWFHNGNL IPTHTQPSYR

FKANNNDSGE YTCQTGQTSL SDPVHLTVLS EWLVLQTPHL EFQEGETIVL RCHSWKDKPL

VKVTFFQNGK SKKFSRSDPN FSIPQANHSH SGDYHCTGNI GYTLYSSKPV TITVQAP.
```

```
                                                           (SEQ ID NO: 11)
QVDTT KAVITLQPPW VSVFQEETVT LHCEVLHLPG SSSTQWFLNG TATQTSTPSY

RITSASVNDS GEYRCQRGLS GRSDPIQLEI HRGWLLLQVS SRVFTEGEPL ALRCHAWKDK

LVYNVLYYRN GKAFKFFHWN SNLTILKTNI SHNGTYHCSG MGKHRYTSAG ISVTVKELFP

APVLNASVTS PLLEGNLVTL SCETKLLLQR PGLQLYFSFY MGSKTLRGRN TSSEYQILTA

RREDSGLYWC EAATEDGNVL KRSPELELQV LGLQLPTP.
```

The Fc receptor was expressed with a signal peptide that is cleaved from the N terminus and the remaining molecule is the extracellular domain less 4 residues on the C terminus (Gln16 Pro288).

Fc-gamma receptor (2.09 ml of in PBS at 0.483 mg/ml) was added to 0.42 ml of activated NHS Sepharose 4 Fast Flow resin (17-0906-01, GE) and allowed to react for 180 minutes at room temperature. The reaction was quenched with 100 mM TRIS pH 8.5. The coupling efficiency, determined using size exclusion chromatography, was 95%. The resin was packed to 0.38 mL in a 0.5 cm ID GE healthcare column and flushed with 10 mls of 100 mM Tris pH 8.5 followed by 10 mls of 100 mM Acetate pH 4.0 with 500 mM NaCl. This was repeated twice and the column was stored in 16% ethanol, 150 mM NaCl 50 mM Tris pH 7.7.

The column was flushed with PBS and loaded at 0.15 ml/min (2.5 min residence time) with 5 ml of 2.0 mg/ml mAb2 in PBS buffer (26.3 mg protein/ml resin). The column was then flushed with 9 ml of PBS at 1 ml/min and eluted with 12 ml of 150 mM Glycine pH 3.0 and 6 ml of 150 mM Glycine pH 2.3 at 1 ml/min. The peak was neutralized with a 15% spike of 1 M MES pH 10.4. The final pool contained 38.6 ug of mAb2 as determined by absorbance at 280 nm. To allow glycan analysis, the mAb2 sample was concentrated to 0.39 mg/ml in 100 microliters using a 30 kD MWCO ultracentrifuge membrane.

To determine the glycan profile of mAb2, approximately 35 μg was digested with PNGase F at 37° C. for 16 hours to release Fc-oligosaccharides. The released N-linked oligosaccharides were labeled with 2-AB for 3 hours at 65° C. Residual 2-AB was removed using acetone precipitation. The oligosaccharide analysis was done on a Xbridge Amide HILIC-HPLC at 45° C. over a linear ammonium formate gradient with fluoresence detection. There was no alteration in the proportion of fucosylated glycoforms in the sample compared to that of the load material. Both the load and the eluted peak had about 5% fucosylated material.

Example 7

This example describes preparation of a C1q medium and use of the medium with mAb2.

C1q is a complement protein that binds to IgG and IgM. Native, human C1q prepared from serum was purchased in pure form from EMD Biosciences, San Diego Calif. (CAS number 80295-33-6).

The C1q (0.85 ml in PBS at 1.17 mg/ml) was added to 0.72 ml of activated NHS Sepharose 4 Fast Flow resin (17-0906-01, GE) and allowed to react for 120 minutes at room temperature. The reaction was quenched with 100 mM TRIS pH 8.5. The coupling efficiency could not be determined by size exclusion chromatography due to the propensity of C1q to aggregate. The resin was packed to 0.64 mL in a 0.5 cm ID column (GE Healthcare) and flushed with 10 mls of 100 mM Tris pH 8.5 followed by 10 mls of 100 mM Acetate pH 4.0 with 500 mM NaCl. This was repeated twice and the column was stored in 16% ethanol, 150 mM NaCl 50 mM Tris pH 7.7.

The column was flushed with PBS and loaded at 0.25 ml/min (2.6 min residence time) with 5 ml of 2.0 mg/ml mAb2 in PBS buffer (15.6 mg protein/ml resin). The column was then flushed with 9 ml of PBS at 1 ml/min and eluted with 12 ml of 150 mM Glycine pH 3.0 at 1 ml/min. The peak was neutralized with a 15% spike of 1 M MES pH 10.4. The final pool contained 7.5 ug of mAb2 as determined by absorbance at 280 nm and size exclusion chromatography. Due to the low amount of mass produced, glycan analysis was not performed.

Example 8

This example describes preparation of a DC-SIGN medium and use of the medium with mAb2.

Some literature indicates that DC-SIGN protein can preferentially bind the sialated glycoforms of antibodies (DC-SIGN and α2,6-sialylated IgG Fc interaction is dispensable for the anti-inflammatory activity of IVIg on human dendritic cells, Bayry, K Bansal, M D Kazatchkine, S V Kaveri; PNAS 2009 106 9 E24). A recombinant human DC-SIGN expressed in NSO-derived cells was purchased in pure form from R&D Systems. The extracellular portion (Lys62 Ala404) was expressed (see GenBank Acc. # Q9NNX6).

DC-SIGN (1 ml in PBS at 0.94 mg/ml) was added to 0.82 ml of activated NHS Sepharose 4 Fast Flow resin (17-0906-01, GE) and allowed to react for 60 minutes at room temperature. The reaction was quenched with 100 mM TRIS pH 8.5. The coupling efficiency, determined using size exclusion chromatography, was 95%. The resin was packed to 0.74 mL in a 0.5 cm ID column (GE Healthcare) and flushed with 10 mls of 100 mM Tris pH 8.5 followed by 10 mls of 100 mM Acetate pH 4.0 with 500 mM NaCl. This was repeated twice and the column was stored in 16% ethanol, 150 mM NaCl 50 mM Tris pH 7.7.

The column was flushed with PBS and loaded at 0.25 ml/min (2.9 min residence time) with 5 ml of 2.0 mg/ml mAb2 in PBS buffer (13.9 mg protein/ml resin). The column was then flushed with 9 ml of PBS at 1 ml/min and eluted with 12 ml 150 mM Glycine pH 3.0 at 1 ml/min. The peak was neutralized with a 15% spike of 1 M MES pH 10.4. This procedure was repeated four times and the five peaks were pooled to produce 128.0 ug of mAb2 as determined by absorbance at 280 nm and size exclusion chromatography. To allow glycan analysis, the mAb2 sample was concentrated to 1.02 mg/ml in 125 microliters using a 30 kD MWCO ultracentrifuge membrane.

To determine the glycan profile of mAb2, approximately 35 μg was digested with PNGase F at 37° C. for 16 hours to release Fc-oligosaccharides. The released N-linked oligosaccharides were labeled with 2-AB for 3 hours at 65° C. Residual 2-AB was removed using acetone precipitation. The oligosaccharide analysis was done on a Xbridge Amide HILIC-HPLC at 45° C. over a linear ammonium formate gradient with fluoresence detection. There was no alteration in the proportion of fucosylated glycoforms in the sample compared to that of the load material. Both the load and the eluted peak had about 5% fucosylated material.

Given DC-SIGN has a $Ca^{++}$ dependent binding domain, an attempt was made to analyze whether calcium in the load could affect binding of mAb2. The column was flushed with 50 mM MES 150 mM NaCl pH 6.5 20 mM $CaCl_2$ and loaded at 0.25 ml/min (3.0 min residence time) with 5 ml of 2.0 mg/ml mAb2 in 50 mM MES 150 mM NaCl pH 6.5 20 mM $CaCl_2$ (13.5 mg protein/ml resin). The column was then flushed with 9 ml of 50 mM MES 150 mM NaCl pH 6.5 20 mM $CaCl_2$ at 1 ml/min. Three elutions were attempted: 6 ml of 50 mM MES 150 mM NaCl pH 6.5; 6 ml of 50 mM MES 150 mM NaCl pH 6.5 20 mM EDTA and 6 ml of 150 mM Glycine pH 2.3 at 1 ml/min. None of the alternative elution conditions had a peak larger than the one obtained with 150 mM Glycine pH 3.0. Thus, the presence of calcium in the load, and variations in elution conditions did not appear to affect binding or recovery in this study.

Example 9

This example describes preparation of an Fc gamma RIIIa receptor medium and ligand density optimization using the medium with mAb2.

Fc gamma RIIIa was obtained from R&D systems. The receptor has the following sequence and a 6-His tag (SEQ ID NO: 16) (see also GenBank Acc. No. AAH17865, P08637 [UniParc]):

(SEQ ID NO: 12)
GMRT EDLPKAVVFL EPQWYRVLEK DSVTLKCQGA YSPEDNSTQW FHNESLISSQ

ASSYFIDAAT VDDSGEYRCQ TNLSTLSDPV QLEVHIGWLL LQAPRWVFKE EDPIHLRCHS

WKNTALHKVT YLQNGKGRKY FHHNSDFYIP KATLKDSGSY FCRGLFGSKN VSSETVNITI

TQGLAVSTIS SFFPPGYQHHHHHH.

The receptor was expression in an NSO-derived cell line. The polypeptide does not have the signal peptide (residues 1-16) and has extracellular residues Gly17-Gln208.

Microliter scale ligand coupling experiments were performed to optimize the ligand density using Fc gamma RIIIA. Six aliquots of 25 ul of activated NHS Sepharose™ 4 Fast Flow resin (17-0906-01, GE) were added to 800 ul wells of a 96 well plate with a 0.45 um polypropylene filter on the bottom (Seahorse Labware F20023). The resin was washed and activated with 700 ul of 1 mM HCl and spun down at 1200×G for 3 minutes. This was repeated for a total of three wash cycles. Varying volumes of 0.66 ug/ul Fc gamma RIIIA were added to the 25 ul of activated resin in each well to evaluate ligand densities between 1.5-9.6 ug-Fc gamma RIIIA/ul-NHS resin including a control well where no Fc gamma RIIIA was added (naïve resin). During the reaction, the plate was agitated on a Tecan Teshake at 1200 rpm for 2 hours at room temperature.

After the reaction, the resin was washed with 700 ul of 100 mM Tris pH 8.3. This was repeated for a total of 2 cycles. Following the Tris wash, 700 ul of 100 mM Acetate pH 4.0 was used. Then 700 ul of 100 mM Tris pH 8.3 was added to each well again to further quench the reaction and the plate was chilled to 2-8° C. for storage. After approximately 15 hrs, the resin was washed twice with 700 ul of 1 mM HEPES pH 7.3. mAb2 which was previously enriched to approximately 45% afucosylated species using a larger scale 0.6 mL column packed with Fc gamma RIIIA immobilized on activated NHS Sepharose™ 4 Fast Flow resin was used as the load material for the batch-bind experiments. Approximately 100 ul of 0.88 ug/ul mAb2 was added to each well and the mixture was agitated on the Teshake at 1200 rpm for 20 minutes. After the load step, the plate was spun down and the flow-through was collected. The resin was then washed with 700 ul of 1 mM HEPES pH 7.2. The resin was then eluted 3 times with 100 ul of 150 mM Glycine pH 3.0. The load, flow-through, wash, and elution fractions were collected with a 96-well plate and measured using UV at 280 and 320 nm.

The results are shown in Table 3. As expected, the naive resin did not exhibit significant protein binding. The mAb2 capacity of the micro well resin preparation was similar to that of the larger resin volume preparation that was used in the packed column (0.17 ug/ul vs. 0.20 ug/ul). The percent utilization was calculated by first dividing the measured mAb2 capacity by the Fc gamma RIIIA ligand density and then dividing this value by the theoretical value at saturation capacity. If one antibody was bound on each Fc gamma RIIIA molecule, then 3.5 ug of antibody would be bound per ug of Fc gamma RIIIA. The best utilization was approximately 10%. The optimal ligand density in terms of total mAb2 capacity per ul of resin and in terms of percent utilization is between 3-7.5 ug/ul. In some embodiments, a medium is prepared and used so as to maximize capacity (e.g., to obtain the most material from a load fluid). In some embodiments, a medium is prepared and used to maximize utilization of Fc receptor. In some embodiments, a medium is prepared and used so as to maximize both capacity and utilization.

TABLE 3

FcγRIIIA media optimization using micro-liter resin preparation.

| ligand density [ug/ul] | Preparation | Capacity [ug-mAb2/ul] | Cap ug-mAb2/ ug-Fc | % Utilization |
|---|---|---|---|---|
| 1.6 | large volume (ml) | 0.17 | 0.11 | 3.1 |
| 1.5 | micro well (ul) | 0.20 | 0.13 | 3.8 |
| 3 | micro well (ul) | 0.91 | 0.30 | 8.6 |
| 5 | micro well (ul) | 1.44 | 0.29 | 8.2 |
| 7.5 | micro well (ul) | 1.63 | 0.22 | 6.2 |
| 9.5 | micro well (ul) | 1.34 | 0.14 | 4.0 |
| 0 (naïve resin) | micro well (ul) | 0.04 | N/A | N/A |

Example 10

This example describes preparation of an Fc gamma RIIIb receptor medium and use of the medium with mAb2.

Fc gamma RIIIB receptor binds to IgG1 and other IgG subclasses. The extracellular domain of the Fc gamma RIIIB receptor was obtained from R&D Systems. This receptor was expressed in NSO-derived cells and includes a C-terminal 10-his tag (SEQ ID NO: 15), This receptor has the following amino acid sequence (see also GenBank Accession #O75015; the sequence includes Thr20-Gln208):

The receptor was expression in an NSO-derived cell line. The polypeptide does not have the signal peptide (residues 1-16) and has extracellular residues Gly17-Gln208.

```
                                                        (SEQ ID NO: 13)
         T EDLPKAVVFL EPQWYSVLEK DSVTLKCQGA YSPEDNSTQW FHNESLISSQ

ASSYFIDAAT VNDSGEYRCQ TNLSTLSDPV QLEVHIGWLL LQAPRWVFKE EDPIHLRCHS

WKNTALHKVT YLQNGKDRKY FHHNSDFHIP KATLKDSGSY FCRGLVGSKN VSSETVNITI

TQGLAVSTIS SFSPPGYQ
```

Fc gamma receptor in PBS (0.54 ml of at 1.87 mg/ml was added to 0.54 ml of activated NHS Sepharose 4 Fast Flow resin (17-0906-01, GE) and allowed to react for 60 minutes at room temperature. The reaction was quenched with 100 mM TRIS pH 8.5. The resin was packed to 0.5 mL in a 0.5 cm ID column (GE Healthcare) and flushed with 10 mls of 100 mM Tris pH 8.5 followed by 10 mls of 100 mM Acetate pH 4.0 with 500 mM NaCl. This was repeated twice and the column was stored in 16% ethanol, 150 mM NaCl 50 mM Tris pH 7.7.

The column was flushed with PBS and loaded at 0.25 ml/min (2.0 min residence time) with 5 ml of 1.96 mg/ml mAb2 in PBS buffer (19.6 mg protein/ml resin). The column was then flushed with 9 ml of PBS at 1 ml/min and eluted with 12 ml of 150 mM Glycine pH 3.0 at 1 ml/min. The peak was neutralized with a 15% spike of 1 M MES pH 10.4. This procedure was repeated three times and the four peaks were pooled to produce 78 ug of mAb2 as determined by absorbance at 280 nm. To allow glycan analysis, the mAb2 sample was concentrated to 0.39 mg/ml in 200 microliters using a 30 kD MWCO ultracentrifuge membrane.

To determine the glycan profile of mAb2, approximately 35 μg was digested with PNGase F at 37° C. for 16 hours to release Fc-oligosaccharides. The released N-linked oligosaccharides were labeled with 2-AB for 3 hours at 65° C. Residual 2-AB was removed using acetone precipitation. The oligosaccharide analysis was done on a Xbridge Amide HILIC-HPLC at 45° C. over a linear ammonium formate gradient with fluoresence detection. The starting mAb2 material had 5.9% non-fucosylated IgG. After enrichment using the Fc receptor column, the mAb2 material had about 39.3% non-fucosylated IgG.

Example 11

This example describes preparation of an Fc gamma RIIIa receptor medium and use of the medium with mAb2.

Fc gamma RIIIa was obtained from R&D systems. The receptor has the following sequence and a 6-His tag (SEQ ID NO: 16) (see also GenBank Acc. No. AAH17865, P08637 [UniParc]):

The Fc-gamma receptor (1.3 ml in PBS at 0.81 mg/ml) was added to 0.64 ml of activated NHS Sepharose™ 4 Fast Flow resin (17-0906-01, GE) and allowed to react for 65 minutes at room temperature. The reaction was quenched with 100 mM TRIS pH 8.3. The coupling efficiency, determined using size exclusion chromatography, was 93%. The resin was packed to 0.55 mL in a 0.5 cm internal diameter (ID) column (GE Healthcare) and flushed with 10 mls of 100 mM Tris pH 8.3 followed by 10 mls of 100 mM Acetate pH 4.0 with 500 mM NaCl. This flushing was repeated twice and the column was stored in 16% ethanol, 150 mM NaCl 50 mM Tris pH 7.7.

The column was flushed with PBS at 1.0 ml/min and loaded at 0.15 ml/min (3.7 min residence time) with 1.0 ml of 0.77 mg/ml mAb2 in PBS buffer (1.4 mg protein/ml resin). The mAb2 material was obtained from a conventional ultrafiltration pool that results from a full purification process using the following: protein A chromatography column, an anion exchange chromatography column, a virus-retaining filter (e.g., a Planova 20 filter (Asahi Kasei Corporation, Tokyo, Japan)), and an ultrafilter.

The Fc receptor column was then flushed with 12 ml of PBS at 1.0 ml/min and eluted with 150 mM Glycine pH at 1.0 ml/min. This procedure was repeated 28 times. The total elution pool had 1.8 mg and the flow through 15.6 mg as determined by absorbance at 280 nm.

To determine the glycan profile of mAb2, approximately 35 μg of IgG from the flow through pool was digested with PNGase F at 37° C. for 16 hours to release Fc-oligosaccharides. The released N-linked oligosaccharides were labeled with 2-AB for 3 hours at 65° C. Residual 2-AB was removed using acetone precipitation. The oligosaccharide analysis was done on a Xbridge Amide HILIC-HPLC at 45° C. over a linear ammonium formate gradient with fluorescence detection.

The starting mAb2 material had 5.4% non-fucosylated and 1.9% mannosylated Fc. The Fc receptor column preferentially bound non-fucosylated and mannosylated IgG Fc. The mAb2 flowing through the column was depleted of non-fucosylated and mannosylated IgG Fc. The mAb2 flow through material had 2.1% non-fucosylated and 1.1% mannosylated IgG Fc. The glycan profile of the material that bound to the Fc receptor column was not measured in this case.

```
                                                        (SEQ ID NO: 14)
       GMRT EDLPKAVVFL EPQWYRVLEK DSVTLKCQGA YSPEDNSTQW

FHNESLISSQ ASSYFIDAAT VDDSGEYRCQ TNLSTLSDPV QLEVHIGWLL LQAPRWVFKE

EDPIHLRCHS WKNTALHKVT YLQNGKGRKY FHHNSDFYIP KATLKDSGSY FCRGLFGSKN

VSSETVNITI TQGLAVSTIS SFFPPGYQHHHHHH
```

Those skilled in the art will recognize, or be able to ascertain using no more than routine experimentation, many equivalents to the specific embodiments of the present disclosure are described herein. The scope of the present disclosure is not intended to be limited to the above Description. Alternative methods and materials and additional applications will be apparent to one of skill in the art, and are intended to be included within the following claims:

We claim:

1. A method of separating afucosylated glycoforms of a polypeptide in a load fluid, the method comprising:
(a) providing a medium comprising an immunoglobulin Fc receptor, wherein the Fc receptor comprises an extracellular domain of an Fc gamma RIII receptor comprising either an amino acid sequence as set forth in residues 21-208 of SEQ ID NO: 1, wherein F176 is changed to V176, or an amino acid sequence as set forth in residues 20-208 of SEQ ID NO: 2; and wherein the medium comprises the immunoglobulin Fc receptor at a density of about 0.01 mg/mL to about 15 mg/mL;
(b) contacting the medium with a load fluid comprising the polypeptide under conditions in which the polypeptide binds to the immunoglobulin Fc receptor, wherein the polypeptide comprises an immunoglobulin Fc receptor binding moiety that is monomeric, wherein the load fluid comprises a plurality of glycoforms of the polypeptide, and wherein the Fc receptor preferentially binds to monomeric afucosylated glycoforms of the polypeptide with an affinity which is at least 2 fold greater than the affinity with which the Fc receptor binds to fucosylated glycoforms of the polypeptide;
(c) contacting the medium with an elution solution under conditions in which the bound polypeptide elutes from the medium; and
(d) recovering the bound polypeptide that elutes from the medium, thereby producing an eluate, wherein the percentage of afucosylated glycoforms of the polypeptide present in the eluate is at least 2-fold greater than the percentage of afucosylated glycoforms of the polypeptide present in the load fluid prior to being contacted with the medium, thereby separating afucosylated glycoforms of the polypeptide in the load fluid.

2. The method of claim 1, wherein the load fluid comprises a cell culture medium.

3. The method of claim 1, wherein the load fluid comprises a fluid that has been purified by one or more ion exchange chromatography steps.

4. The method of claim 1, wherein the load fluid comprises a pharmaceutical drug product or drug substance.

5. The method of claim 1, wherein the immunoglobulin Fc receptor binding moiety comprises an immunoglobulin Fc region.

6. The method of claim 1, wherein the polypeptide comprises an antibody.

7. The method of claim 1, wherein the polypeptide comprises an Fc fusion protein.

8. The method of claim 1, wherein the polypeptide comprises one or more polypeptides selected from the group consisting of single domain antibodies, maxibodies, minibodies, intrabodies, small modular immunopharmaceuticals (SMIPs), IgG-scFv bispecific antibodies, antibody-peptide fusions, antibody-drug fusions, and Fc receptor binding polypeptides on a virus or virus capsid.

9. The method of claim 1, wherein the polypeptide is produced in a fungal cell.

10. The method of claim 1, wherein the polypeptide is produced in an insect cell.

11. The method of claim 1, wherein the polypeptide is produced in a plant cell.

12. The method of claim 1, wherein the Fc receptor comprises a full length Fc gamma RIII receptor.

13. The method of claim 1, wherein the percentage of the afucosylated glycoforms of the polypeptide in the eluate is increased by at least 5-fold, 10-fold, or 20-fold, relative to the percentage of afucosylated glycoforms of the polypeptide present in the load fluid prior to being contacted with the medium.

14. The method of claim 1, wherein the eluate comprises one or more fractions of bound polypeptide eluted from the medium.

15. The method of claim 1, further comprising fractionating the eluate.

16. The method of claim 1, wherein the medium comprises beads, membranes, monoliths, a fiber matrix, porous media, or a gel.

17. The method of claim 1, wherein the medium comprises agarose, cellulose, dextran, ceramic, metal, glass, polytetrafluoroethylene, nylon, polycarbonate, polyacrylamide, polystyrene, polypropylene, polyether sulfone, polyamide, polysulfone, polyester, polyvinylidene fluoride, a fluorocarbon, polyethylene, polyacrylate, or poly(azolactone).

18. The method of claim 1, wherein the Fc receptor is linked to the medium via a crosslinker or enzyme-mediated coupling.

19. The method of claim 1, wherein the Fc receptor is linked to the medium via a disulfide bond, metal chelation, cyanogen bromide, an NHS linkage, a histidine tag, a glycidyl ether, an epoxy, a tresyl chloride linkage, a tosyl chloride linkage, an EAH linkage, an ECH linkage, an activated thiol linkage, or a thiopropyl linkage.

20. The method of claim 1, further comprising contacting the medium with an equilibration solution comprising between 1 and 500 mM of a buffer, and between 0 and 2000 mM of a salt, at a pH between 3.5 and 10, prior to contacting the medium with the load fluid.

21. The method of claim 1, wherein the load fluid comprises the polypeptide at a concentration between 0.001 and 100 mg/mL.

22. The method of claim 1, wherein the amount of polypeptide present in the load fluid that is contacted with the medium ranges from 0.1 to 25,000 mg polypeptide/mL medium.

23. The method of claim 1, wherein the elution solution has a pH between 2 and 5 and between 0 and 2000 mM of a salt, and optionally, an additive, and optionally, a solvent.

24. The method of claim 1, wherein the medium is contacted with one or more elution solutions under conditions in which a pH gradient is applied.

25. The method of claim 1, further comprising neutralizing the eluate.

26. The method of claim 1, further comprising producing a pharmaceutical composition from the polypeptide in the eluate.

27. The method of claim 1, wherein the load fluid comprises serum IgG.

28. The method of claim 1, wherein the percentage of immunoglobulin Fc receptor binding moiety that is monomeric in the eluate is at least about 70%, about 80%, about 90%, about 95%, or about 99%.

29. The method of claim 1, wherein the extracellular domain of the Fc gamma RIII receptor consists essentially of residues 17-208 of SEQ ID NO: 1, wherein F176 is changed to V176.

30. The method of claim 29, wherein the Fc gamma RIII receptor is linked to the medium via a histidine tag.

31. The method of claim 1, consisting essentially of:
(a) providing a medium comprising an immunoglobulin Fc receptor, wherein the Fc receptor comprises an extracellular domain of an Fc gamma RIII receptor comprising either an amino acid sequence as set forth in residues 21-208 of SEQ ID NO: 1, wherein F176 is changed to V176, or an amino acid sequence as set forth in residues 20-208 of SEQ ID NO: 2; and wherein the medium comprises the immunoglobulin Fc receptor at a density of about 0.01 mg/mL to about 15 mg/mL;
(b) contacting the medium with a load fluid comprising the polypeptide under conditions in which the polypeptide binds to the immunoglobulin Fc receptor, wherein the polypeptide comprises an immunoglobulin Fc receptor binding moiety that is monomeric, wherein the load fluid comprises a plurality of glycoforms of the polypeptide, and wherein the Fc receptor preferentially binds to monomeric afucosylated glycoforms of the polypeptide with an affinity which is at least 2 fold greater than the affinity with which the Fc receptor binds to fucosylated glycoforms of the polypeptide;

(c) contacting the medium with an elution solution under conditions in which the bound polypeptide elutes from the medium; and (d) recovering the bound polypeptide that elutes from the medium, thereby producing an eluate, wherein the percentage of afucosylated glycoforms of the polypeptide present in the eluate is at least 2-fold greater than the percentage of afucosylated glycoforms of the polypeptide present in the load fluid prior to being contacted with the medium, thereby separating afucosylated glycoforms of the polypeptide in the load fluid.

32. The method of claim 31, consisting of:

(a) providing a medium comprising an immunoglobulin Fc receptor, wherein the Fc receptor comprises an extracellular domain of an Fc gamma RIII receptor comprising either an amino acid sequence as set forth in residues 21-208 of SEQ ID NO: 1, wherein F176 is changed to V176, or an amino acid sequence as set forth in residues 20-208 of SEQ ID NO: 2; and wherein the medium comprises the immunoglobulin Fc receptor at a density of about 0.01 mg/mL to about 15 mg/mL;

(b) contacting the medium with a load fluid comprising the polypeptide under conditions in which the polypeptide binds to the immunoglobulin Fc receptor, wherein the polypeptide comprises an immunoglobulin Fc receptor binding moiety that is monomeric, wherein the load fluid comprises a plurality of glycoforms of the polypeptide, and wherein the Fc receptor preferentially binds to monomeric afucosylated glycoforms of the polypeptide with an affinity which is at least 2 fold greater than the affinity with which the Fc receptor binds to fucosylated glycoforms of the polypeptide;

(c) contacting the medium with an elution solution under conditions in which the bound polypeptide elutes from the medium; and (d) recovering the bound polypeptide that elutes from the medium, thereby producing an eluate, wherein the percentage of afucosylated glycoforms of the polypeptide present in the eluate is at least 2-fold greater than the percentage of afucosylated glycoforms of the polypeptide present in the load fluid prior to being contacted with the medium, thereby separating afucosylated glycoforms of the polypeptide in the load fluid.

33. The method of claim 1, wherein the medium comprises the immunoglobulin Fc receptor at a density of between about 0.1 mg/mL to about 10 mg/mL.

34. The method of claim 33, wherein the medium comprises the immunoglobulin Fc receptor at a density of between about 1 mg/mL to about 7.5 mg/mL.

35. The method of claim 1, wherein the method includes contacting the medium with one or more wash solutions, prior to contacting the medium with the elution solution.

36. The method of claim 35, wherein the one or more wash solutions are at a pH between 3.5 and 10 and comprise between 1 and 500 mM of a buffer, and between 0 and 2000 mM of a salt, and optionally, an additive, and optionally, a solvent.

37. The method of claim 1, further comprising analyzing a characteristic of the polypeptide eluted from the medium.

38. The method of claim 37, wherein oligosaccharides from the polypeptide are analyzed.

39. The method of claim 37, wherein a biological activity of the polypeptide is analyzed.

40. The method of claim 37, wherein the analyzed characteristic of the polypeptide eluted from the medium comprises one or more of toxicity, stability, or efficacy.

41. The method of claim 37, further comprising analyzing the polypeptide in the load fluid or polypeptide that has flowed through the medium.

42. The method of claim 1, wherein the method includes recovering the polypeptide that flows through the medium.

43. The method of claim 42, further comprising producing a pharmaceutical composition from the polypeptide that has flowed through the medium.

44. The method of claim 42, wherein a biological activity of the polypeptide that has flowed through the medium is altered, relative to the activity of the polypeptide in the load fluid.

45. The method of claim 42, wherein the method comprises analyzing the polypeptide that has flowed through the medium.

46. The method of claim 45, wherein oligosaccharides on the polypeptide are analyzed.

47. The method of claim 45, wherein the analyzed characteristic of the polypeptide that has flowed through the medium comprises one or more of toxicity, stability, or efficacy.

48. The method of claim 45, wherein a biological activity of the polypeptide that has flowed through the medium is analyzed.

49. The method of claim 1, further comprising contacting the eluate with a second medium, and recovering polypeptide that flows through, or is eluted from, the second medium.

50. The method of claim 49, wherein the second medium comprises an ion exchange medium, a hydroxyapatite medium, a protein A medium, a hydrophobic interaction medium, an immobilized metal affinity medium, a synthetic medium, a lectin, or a combination thereof.

51. The method of claim 42, wherein the method includes loading the medium at 5-1900% of the polypeptide capacity of the medium.

52. The method of claim 1, wherein the polypeptide is produced in a mammalian cell.

53. The method of claim 52, wherein the polypeptide is produced in a CHO cell.

54. The method of claim 52, wherein the polypeptide is produced in an NSO cell.

55. The method of claim 52, wherein the polypeptide is produced in an Sp2/0 cell.

56. The method of claim 1, wherein a biological activity of polypeptide in the eluate is altered relative to the activity of the polypeptide in the load fluid.

57. The method of claim 56, wherein the biological activity comprises antibody dependent cell mediated cytotoxicity (ADCC), and wherein ADCC is increased.

* * * * *